US012697428B2

(12) United States Patent
Locke et al.

(10) Patent No.: US 12,697,428 B2
(45) Date of Patent: Aug. 4, 2026

(54) WOUND FLUID COLLECTION CANISTER WITH INTEGRATED IRRIGATION FLUID PUMP HEAD

(71) Applicant: Solventum Intellectual Properties Company, Maplewood, MN (US)

(72) Inventors: Christopher B. Locke, Bournemouth (GB); Benjamin A. Pratt, Poole (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 448 days.

(21) Appl. No.: 18/018,717

(22) PCT Filed: Jul. 20, 2021

(86) PCT No.: PCT/IB2021/056536
§ 371 (c)(1),
(2) Date: Jan. 30, 2023

(87) PCT Pub. No.: WO2022/023874
PCT Pub. Date: Feb. 3, 2022

(65) Prior Publication Data
US 2024/0009376 A1     Jan. 11, 2024

Related U.S. Application Data

(60) Provisional application No. 63/058,681, filed on Jul. 30, 2020.

(51) Int. Cl.
A61M 1/00 (2006.01)
A61M 3/02 (2006.01)
(52) U.S. Cl.
CPC ............ A61M 1/98 (2021.05); A61M 3/0258 (2013.01)

(58) Field of Classification Search
CPC .. A61M 1/98; A61M 3/0258; A61M 5/14232; A61M 1/92; A61M 1/77; A61B 2217/007
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| (Continued) | | |

FOREIGN PATENT DOCUMENTS

| | | |
|---|---|---|
| AU | 550575 B2 | 3/1986 |
| AU | 745271 B2 | 3/2002 |
| (Continued) | | |

OTHER PUBLICATIONS

International Search Report and Written Opinion Corresponding to PCT/IB2021/056536, mailed Oct. 5, 2021.
(Continued)

*Primary Examiner* — Guy K Townsend
*Assistant Examiner* — Alessandro R Del Priore

(57) ABSTRACT

A combined installation fluid delivery pump head and wound fluid collection canister apparatus for use with a negative pressure wound therapy (NPWT) unit includes a body defining a wound fluid collection canister configured to collect wound exudate and defining a pump head formed by a partially cylindrical recess in a wall of the body. The apparatus includes a flexible fluid instillation conduit extending along the pump head to be compressed by a pump rotor from the NPWT unit. The apparatus includes a first conduit fluidly coupled on one end of the first conduit to a negative pressure source on the NPWT unit. The apparatus includes a second conduit having one end of the second conduit communicating with the wound fluid collection canister. The apparatus includes a third conduit fluidly coupled to one end of the flexible fluid installation conduit.

4 Claims, 22 Drawing Sheets

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2012/0157750 | A1* | 6/2012 | Robinson ................ A61F 13/05 604/290 |
| 2013/0138059 | A1* | 5/2013 | Malhi ..................... A61M 1/74 604/319 |
| 2014/0163491 | A1 | 6/2014 | Schuessler et al. |
| 2015/0080788 | A1 | 3/2015 | Blott et al. |
| 2018/0361037 | A1 | 12/2018 | Pratt et al. |
| 2019/0275219 | A1 | 9/2019 | Ehlert et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3488879 A1 | 5/2019 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |

(56)                    References Cited

FOREIGN PATENT DOCUMENTS

| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

335

1700

1900

2200

2205 — PROVIDE INSTILLATION AND EXUDATE UNIT

2210 — PROVIDE NEGATIVE PRESSURE WOUND THERAPY UNIT

2215 — COUPLE INSTILLATION AND EXUDATE UNIT TO NPWT UNIT

2220 — SECURE INSTILLATION FLUID CONTAINER TO BODY

2225 — SECURE INSTILLATION FLUID CONTAINER TO SPIKE

WOUND FLUID COLLECTION CANISTER WITH INTEGRATED IRRIGATION FLUID PUMP HEAD

CROSS-REFERENCE TO RELATED APPLICATIONS

This application claims the benefit of priority to U.S. Provisional Application No. 63/058,681, filed on Jul. 30, 2020, which is incorporated herein by reference in its entirety.

TECHNICAL FIELD

The present application relates generally to wound therapy systems and devices, and more particularly to a negative pressure wound therapy device.

BACKGROUND

Negative pressure wound therapy (NPWT) is a type of wound therapy that involves applying negative pressure (relative to atmospheric pressure) to a wound site to promote wound healing. Some NPWT systems include a pump which operates to maintain the wound site at negative pressure by removing wound exudate from the wound site. The wound exudate is typically routed to a canister or other container fluidly connected to the pump where the wound exudate is stored until emptied by a user.

SUMMARY

For a non-healthcare professional, negative pressure wound therapy systems may be challenging to operate. To aid in adoption of NPWT systems, in particular in the home-care space, there exists a need to simplify the therapy application and function such that a low-skilled user may use NPWT systems without overwhelming difficulty.

The systems and methods of the present disclosure offer a combined instillation delivery pump head and wound fluid collection canister in a single disposable system which simplifies the process for connecting the NPWT system to the wound site. The systems described herein allow for collected fluids to be emptied when the wound fluid collection canister is removed from the negative pressure wound therapy unit. This can prolong the life of the wound fluid collection canister. Additionally, different tube conduits can be combined into one multi-conduit tube and wound connection pad which can be easily separated if the user chooses.

At least one aspect of the present disclosure is directed to a combined instillation fluid delivery pump head and wound fluid collection canister apparatus for use with a negative pressure wound therapy unit. The apparatus can include a body defining a wound fluid collection canister configured to collect wound exudate and defining a pump head formed by a partially cylindrical recess in a wall of the body. The apparatus can also include a flexible fluid instillation conduit extending along the pump head to be compressed by a pump rotor from the negative pressure wound therapy unit. A first conduit may be disposed on the body and fluidly coupled on one end of the first conduit to a negative pressure source on the negative pressure wound therapy unit. A second conduit may be disposed on the body and having one end of the second conduit communicating with the wound fluid collection canister. A third conduit may be disposed on the body and fluidly coupled to one end of the flexible fluid instillation conduit.

Another aspect of the present disclosure is directed to an instillation and negative pressure wound therapy apparatus. The apparatus can include an instillation and exudate unit, which can include a body defining a wound fluid collection canister configured to collect wound exudate and defining a pump head formed by a partially cylindrical recess in a wall of the body. A flexible fluid instillation conduit may extend along the pump head to be compressed by a pump rotor. The instillation and exudate unit can include a first conduit disposed on the body to be fluidly coupled on one end of the first conduit to a negative pressure source. A second conduit may be disposed on the body and having one end communicating with the wound fluid collection canister. A third conduit may be disposed on the body and fluidly coupled to one end of the flexible fluid instillation conduit. The instillation and negative pressure wound therapy apparatus can include a negative pressure wound therapy unit coupled to the instillation and exudate unit. The negative pressure wound therapy unit can include a peristaltic pump configured to pump instillation fluid through the third conduit and compress the flexible fluid instillation conduit.

Another aspect of the present disclosure is directed to a method for providing instillation and negative pressure wound therapy. The method can include providing an instillation and exudate unit. The installation and exudate unit can include a body defining a wound fluid collection canister configured to collect wound exudate and defining a pump head formed by a partially cylindrical recess in a wall of the body. A flexible fluid instillation conduit extends along the pump head to be compressed by a pump rotor. The instillation and exudate unit can also include a first conduit disposed on the body and fluidly coupled on one end of the first conduit to a negative pressure source. A second conduit may be disposed on the body and having one end communicating with the wound fluid collection canister. A third conduit may be disposed on the body and fluidly coupled to one end of the flexible fluid instillation conduit. The method can also include providing a negative pressure wound therapy unit coupled to the instillation and exudate unit. The negative pressure wound therapy unit can include a peristaltic pump configured to pump instillation fluid through the third conduit.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The details of one or more implementations of the subject matter described in this specification are set forth in the accompanying drawings and the description below. Other features, aspects, and advantages of the subject matter will become apparent from the description, the drawings, and the claims.

Like reference numbers and designations in the various drawings indicate like elements.

DETAILED DESCRIPTION

Following below are more detailed descriptions of various concepts related to, and implementations of, methods, apparatuses, and systems for instillation and negative pressure wound therapy. The various concepts introduced above and discussed in greater detail below may be implemented in any of a number of ways, as the described concepts are not limited to any particular manner of implementation. Examples of specific implementations and applications are provided primarily for illustrative purposes.

Figure 1:
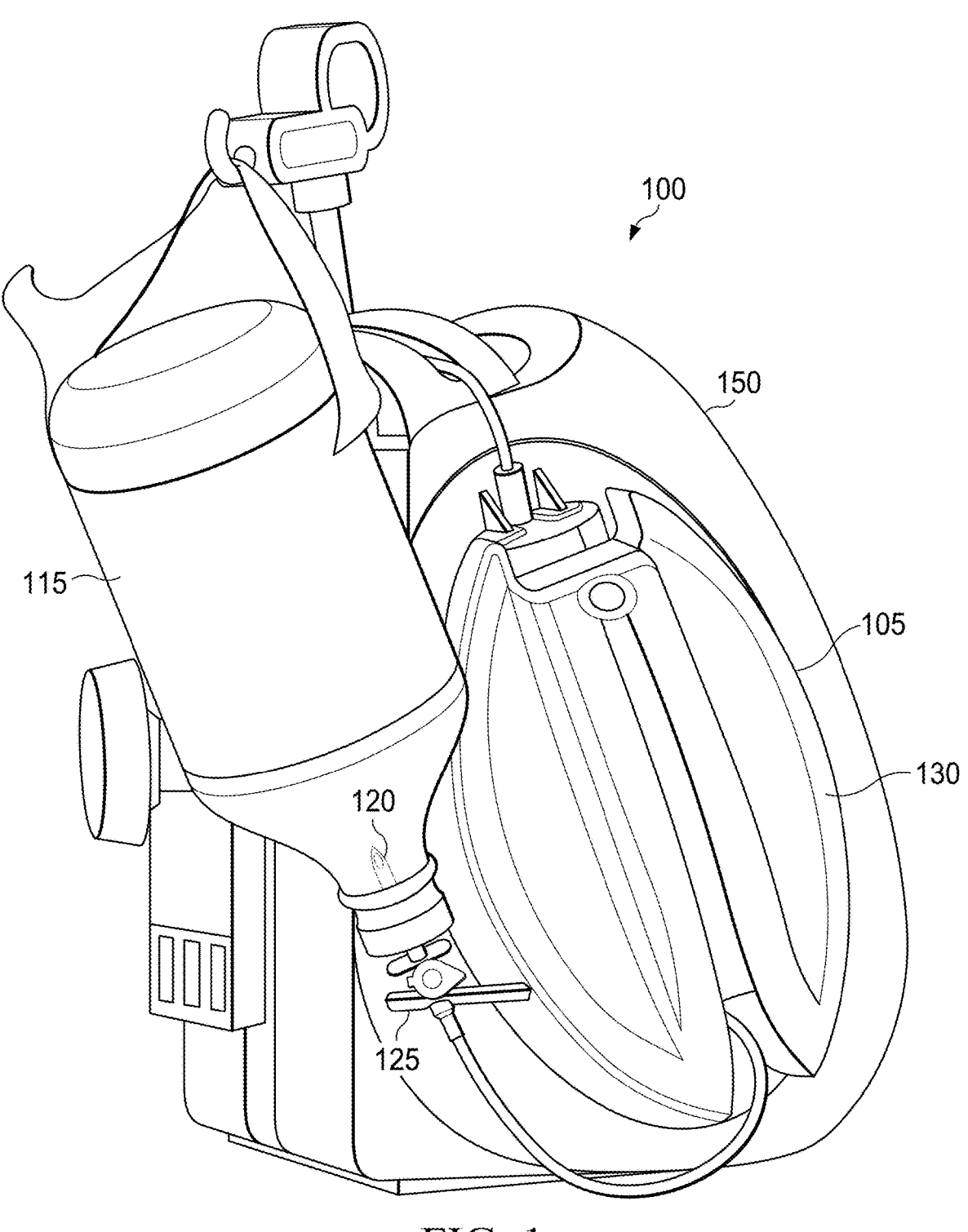
FIG. 1 illustrates a perspective view of an instillation and negative pressure wound therapy apparatus, according to an exemplary embodiment.

FIG. 1 illustrates a perspective view of an installation and negative pressure wound therapy apparatus 100 (e.g., negative pressure wound therapy system). The installation and negative pressure wound therapy apparatus 100 can provide negative pressure wound therapy by reducing pressure at a wound site (e.g., wound). The instillation and negative pressure wound therapy apparatus 100 can draw a vacuum at the wound site by removing wound exudate, air, and other fluids from the wound site. The instillation and negative pressure wound therapy apparatus 100 can include an instillation and exudate unit 105 described herein. The instillation and exudate unit 105 can be an integrated, single piece disposable component.

The instillation and negative pressure wound therapy apparatus 100 can include an instillation fluid container 115 (e.g., instillation fluid bag, instillation container, instillation bag, fluid reservoir, etc.). The instillation fluid container 115 can contain or house instillation fluid. Instillation fluid can include, for example, a cleansing fluid, a prescribed fluid, a medicated fluid, an antibiotic fluid, or any other type of fluid which can be delivered to the wound site during wound treatment. The wound site can include a tissue wound or a wound dressing that covers the tissue wound and adheres to a patient's skin. The instillation fluid container 115 can be oriented such that instillation fluid can flow to the instillation and exudate unit 105 by a pump or by gravity.

The instillation and negative pressure wound therapy apparatus 100 can include a fluid spike 120 (e.g., spike, fluid container connection spike, spike head, integrated fluid storage bag spike, fluid bag connection spike, pre-fitted instillation bag spike, etc.). The fluid spike 120 can be configured to couple (e.g., connect, affix, link, join, etc.) to the instillation fluid container 115. For example, the fluid spike 120 can be removably connected to the instillation fluid container 115. The fluid spike 120 can be configured to pierce (e.g., puncture) the instillation fluid container 115. For example, the fluid spike 120 can pierce the instillation fluid container 115 such that instillation fluid is accessible to the instillation and exudate unit 105. The fluid spike 120 can have a sharp end configured to pierce the instillation fluid container 115. The fluid spike 120 can fluidly couple the instillation fluid container 115 to the instillation and exudate unit 105. The fluid spike 120 can include a cavity configured to allow instillation fluid to flow.

The instillation and negative pressure wound therapy apparatus 100 can include a fluid spike mount 125 (e.g., spike mount, fluid container connection spike mount, etc.) The fluid spike mount 125 can be coupled to a body 130 and can be configured to support a weight of the instillation fluid container 115 on the body 130. The fluid spike mount 125 can secure the instillation fluid container 115 when the instillation fluid container 115 is connected to the fluid spike 120 and can be configured to hold and/or support the fluid spike 120. The fluid spike mount 125 can also include a protrusion connected to the body 130. The fluid spike mount 125 is shown to be disposed on a lower section (e.g., lower half) of the body 130 and can be disposed on an exterior of the body 130. In some embodiments, the fluid spike mount 125 and the body 130 can be integrally formed.

The instillation and negative pressure wound therapy apparatus 100 can include a negative pressure wound therapy unit 150. The negative pressure wound therapy unit 150 can be coupled to the instillation and exudate unit 105. The negative pressure wound therapy unit 150 can include a peristaltic pump (not shown), which can be a positive displacement pump for pumping the instillation fluid from the instillation fluid container 115. The peristaltic pump can be located in an interior of the negative pressure wound therapy unit 150, such that it is disposed between the negative pressure wound therapy unit 150 and the instillation and exudate unit 105. The negative pressure wound therapy unit 150 can support the instillation fluid container 115, and can be fluidly connected to the wound site. The instillation and negative pressure wound therapy apparatus 100 can include an attachment mechanism (e.g., latch) configured to couple the instillation and exudate unit 105 to the negative pressure wound therapy unit 150.

Figure 2:
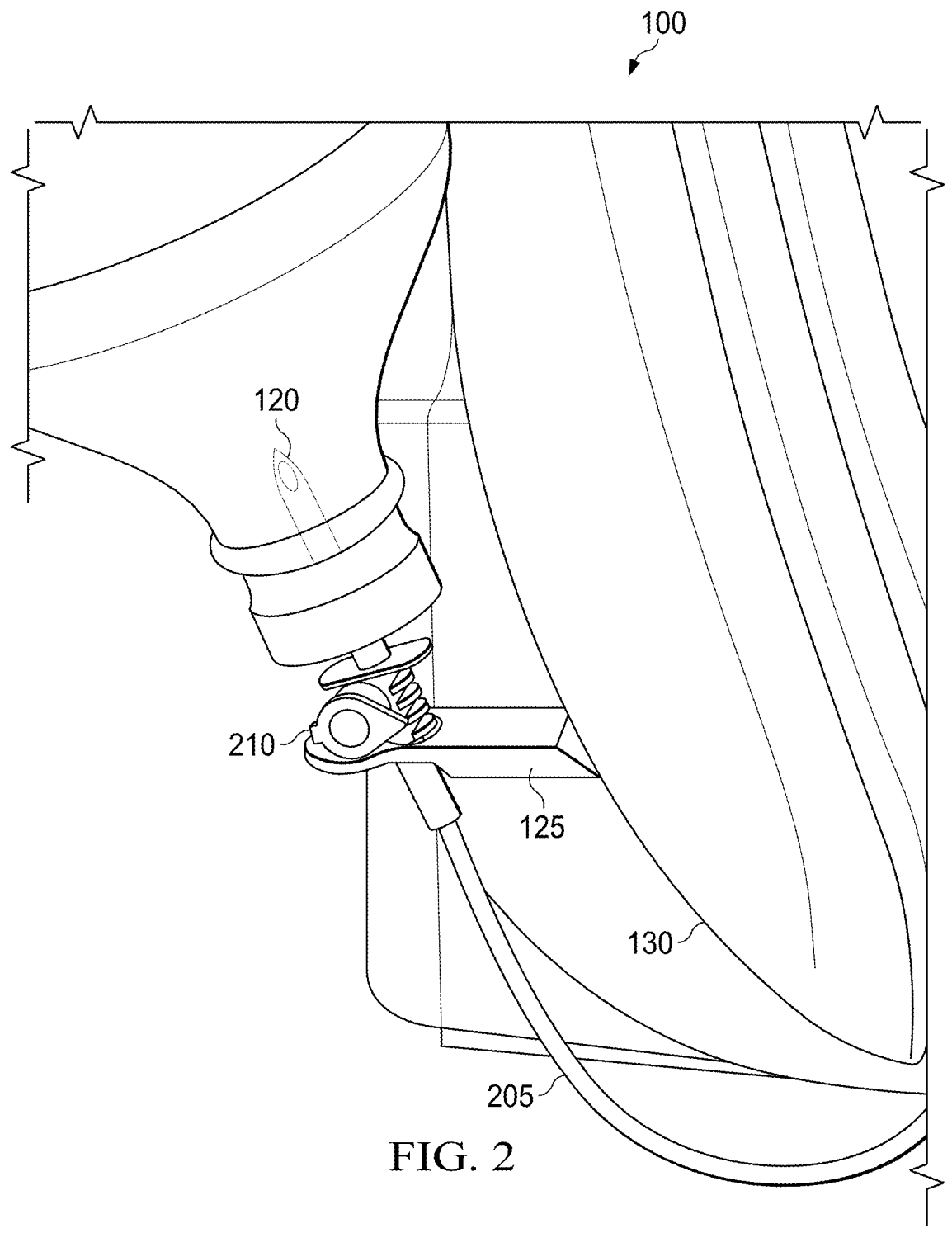
FIG. 2 illustrates a detailed view of the instillation and negative pressure wound therapy apparatus of FIG. 1, according to an exemplary embodiment.

FIG. 2 illustrates a detailed view of the instillation and negative pressure wound therapy apparatus 100 of FIG. 1. The instillation and negative pressure wound therapy apparatus 100 can include the fluid spike 120, the fluid spike mount 125, and the body 130. The instillation and negative pressure wound therapy apparatus 100 can include a fluid spike conduit 205. The fluid spike conduit 205 can couple the fluid spike 120 to the body 130 and allow instillation fluid to flow from the instillation fluid container 115 to the instillation and exudate unit 105. The fluid spike conduit 205 can connect to the fluid spike 120 through a pneumatic connection.

The instillation and negative pressure wound therapy apparatus 100 can include a valve 210. The valve 210 can be configured to control (e.g., regulate, direct, etc.) the flow of instillation fluid from the instillation fluid container 115. The valve 210 can be disposed on the fluid spike 120, or between the fluid spike 120 and the fluid spike conduit 205. The valve 210 is intended to regulate the flow of instillation fluid through the fluid spike conduit 205 (e.g. by opening, closing, or partially obstructing the fluid spike conduit 205).

Figure 3:
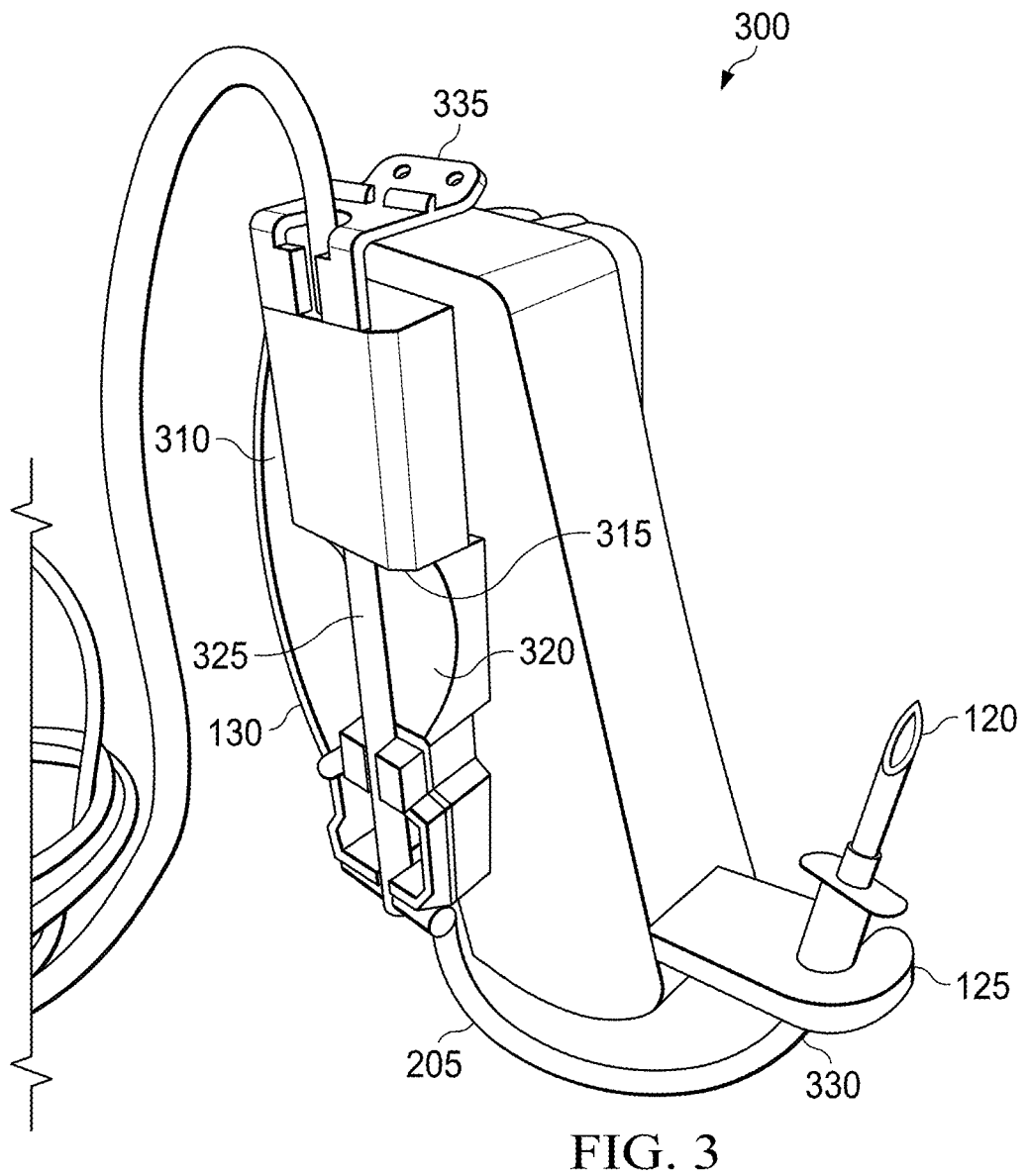
FIGS. 3 and 4 illustrate perspective views of a combined instillation fluid delivery pump head and wound fluid collection canister apparatus, according to an exemplary embodiment.
Figure 4:
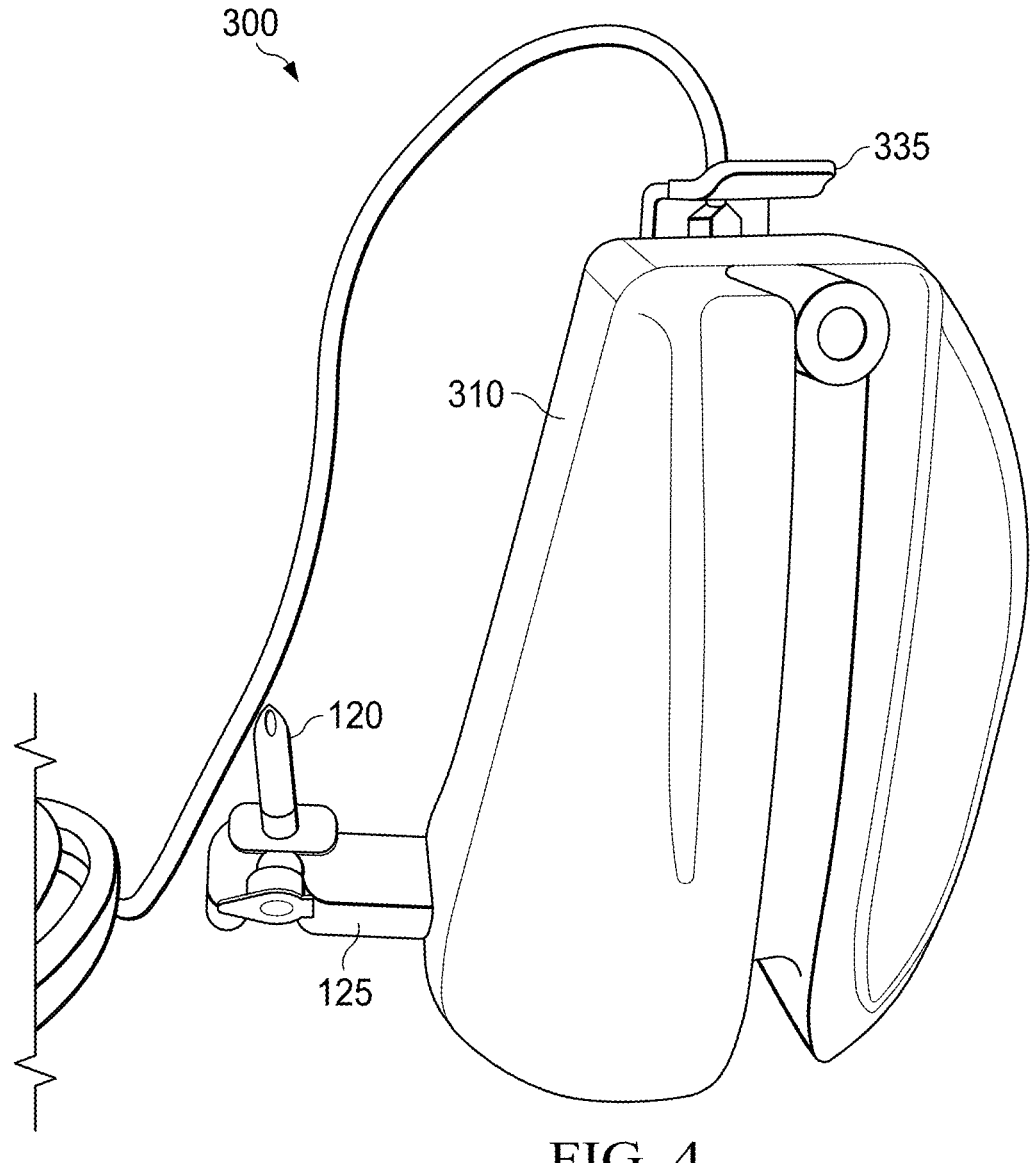

FIGS. 3 and 4 illustrate perspective views of a combined instillation fluid delivery pump head and wound fluid collection canister apparatus 300 (e.g., instillation and exudate unit 105). The combined instillation fluid delivery pump head and wound fluid collection canister apparatus 300 can be used with the negative pressure wound therapy unit 150. The combined instillation fluid delivery pump head and wound fluid collection canister apparatus 300 is shown to include the body 130. The body 130 can define a wound fluid collection canister 310 (e.g., collected fluid container, collected fluid canister, wound fluid collection container, negative pressure wound therapy canister, etc.). The wound fluid collection canister 310 can be configured to collect wound exudate. Wound exudate (e.g., medical waste) can include fluids removed from the wound site, such as fluid that filters from a patient's circulatory system into lesions or areas of inflammation. For example, wound exudate can include water and dissolved solutes such as blood, plasma proteins, white blood cells, platelets, and red blood cells. Other fluids removed from the wound site may include instillation fluid previously delivered to wound site. The wound fluid collection canister 310 and the fluid spike 120 can be an integrated unit. The wound fluid collection canister 310 and the fluid spike 120 can be a disposable unit, which can be a lower quality engineering plastic.

The body 130 is also shown to define a pump head 315 (e.g., integrated delivery pump head, irrigation fluid pump head, etc.) formed by a recess 320 (e.g., partially cylindrical recess, cylindrical recess, etc.) in a wall of the body 130. The wall of the body 130 can have a shape profile configured to mate with a pump rotor (e.g., rotating rollers, vanes or fins extending radially from a hub and driven by a pump motor) and corresponding wall of the negative pressure wound therapy unit 150. The recess 320 can be other shapes, such as circular, spherical, and other polygonal or non-polygonal shapes configured to mate with the pump rotor. The pump rotor is intended to be inserted into the recess 320 when the body 130 is coupled to the negative pressure wound therapy unit 150.

The combined instillation fluid delivery pump head and wound fluid collection canister apparatus 300 is shown to include a flexible fluid instillation conduit 325 extending along the pump head 315. The flexible fluid instillation conduit 325 can include a first flexible fluid instillation conduit end 330 (e.g., first end). The first flexible fluid instillation conduit end 330 can be coupled to a fluid spike 120. For example, the first flexible fluid instillation conduit end 330 can be coupled to the fluid spike conduit 205. A size and a shape of the recess 320 can be configured to provide a predetermined compression of the flexible fluid instillation conduit 325 by the pump rotor when the body 130 is joined to the negative pressure wound therapy unit 150 and the pump rotor engages within the pump head 315. The flexible fluid instillation conduit 325 can span a length of the recess 320.

The flexible fluid instillation conduit 325 can be configured to be compressed by a pump rotor from the negative pressure wound therapy unit 150. The pump rotor can be part of the negative pressure wound therapy unit 150. The pump rotor can include a peristaltic pump disposed on the negative pressure wound therapy unit 150. The peristaltic pump can be configured to compress the flexible fluid instillation conduit 325. The pump rotor can be configured to compress the flexible fluid instillation conduit 325. The pump rotor can include rotating vanes, or one or more rollers attached to an external circumference of the pump rotor. The pump rotor can compress the flexible fluid instillation conduit 325 along its axis on a particular periodic frequency as the pump rotor rotates. Part of the flexible fluid instillation conduit 325 under compression can be occluded in an axial direction toward the wound such that fluid (e.g., instillation fluid) is moved through the flexible fluid instillation conduit 325 toward the wound.

The combined instillation fluid delivery pump head and wound fluid collection canister apparatus 300 can include a latch 335 (e.g., catch, mechanical fastener, etc.). The latch 335 can be configured to couple the body 130 to the negative pressure wound therapy unit 150. For example, the latch 335 can be configured to secure the body 130 to the negative pressure wound therapy unit 150. The latch 335 can be configured to couple the pump head 315 to the pump rotor. The body 130 can be interchangeably detachable from the negative pressure wound therapy unit 150 via the latch 335 for replacement and disposal of the wound fluid collection canister 310 and instillation fluid container 115 as a single unit (e.g., integrated unit, single piece, etc.). For example, the latch 335 can join the body 130 to the negative pressure wound therapy unit 150. The latch 335 can join the body 130 to the wound fluid collection canister 310. The latch 335 can secure the body 130 to the wound fluid collection canister 310. The latch 335 can also position the flexible fluid instillation conduit 325 at the pump head 315.

Figure 5:
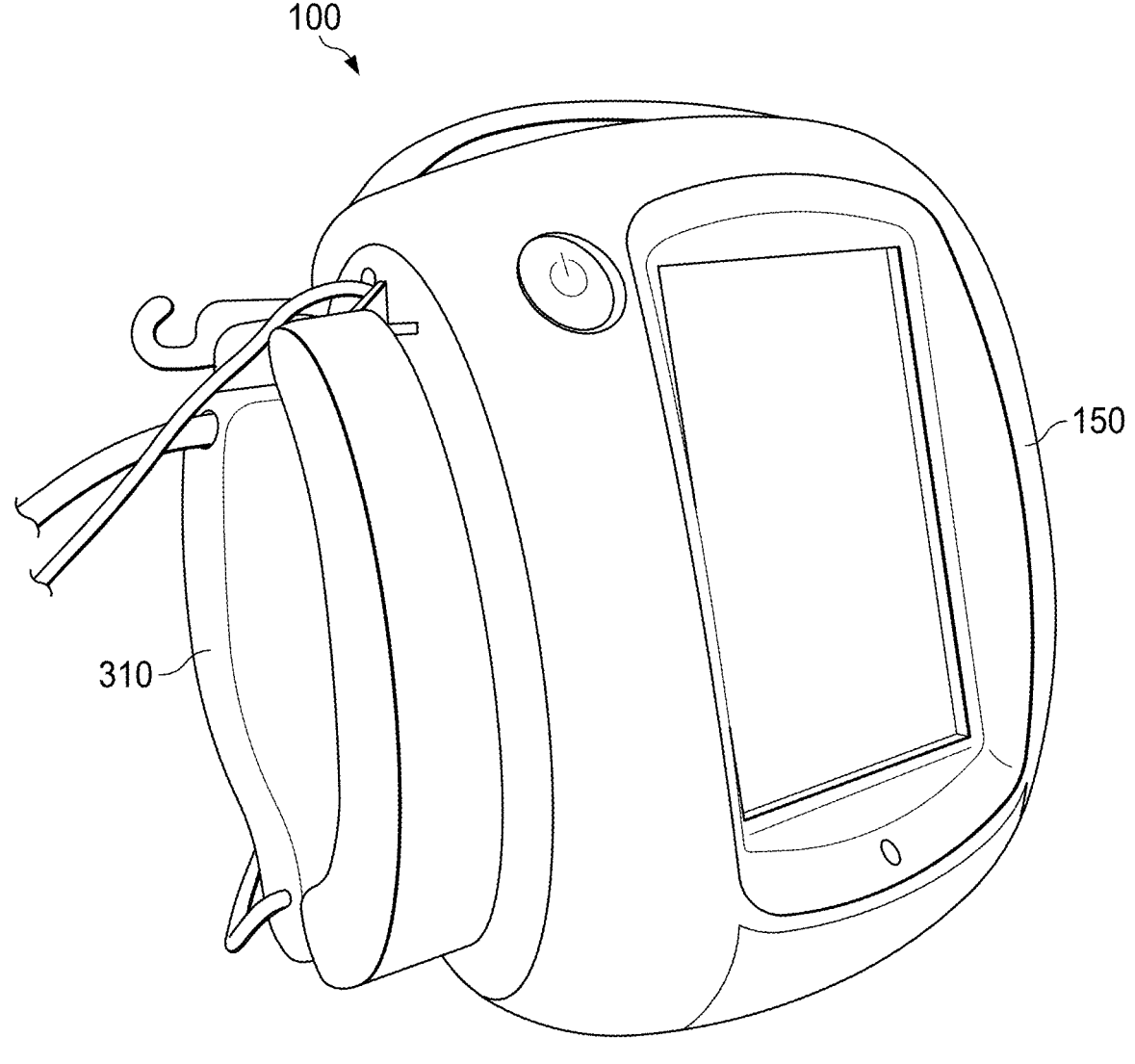
FIG. 5 illustrates a perspective view of an installation and negative pressure wound therapy apparatus, according to an exemplary embodiment.

FIG. 5 illustrates a perspective view of an instillation and negative pressure wound therapy apparatus 100. The instillation and negative pressure wound therapy apparatus 100 can include the negative pressure wound therapy unit 150 and the wound fluid collection canister 310. The negative pressure wound therapy unit 150 can include a screen (e.g., display screen, graphical user interface, etc.) configured to display information. For example, information related to pressure, flow rate, filtration quality, wound exudate composition can be displayed.

Figure 6:
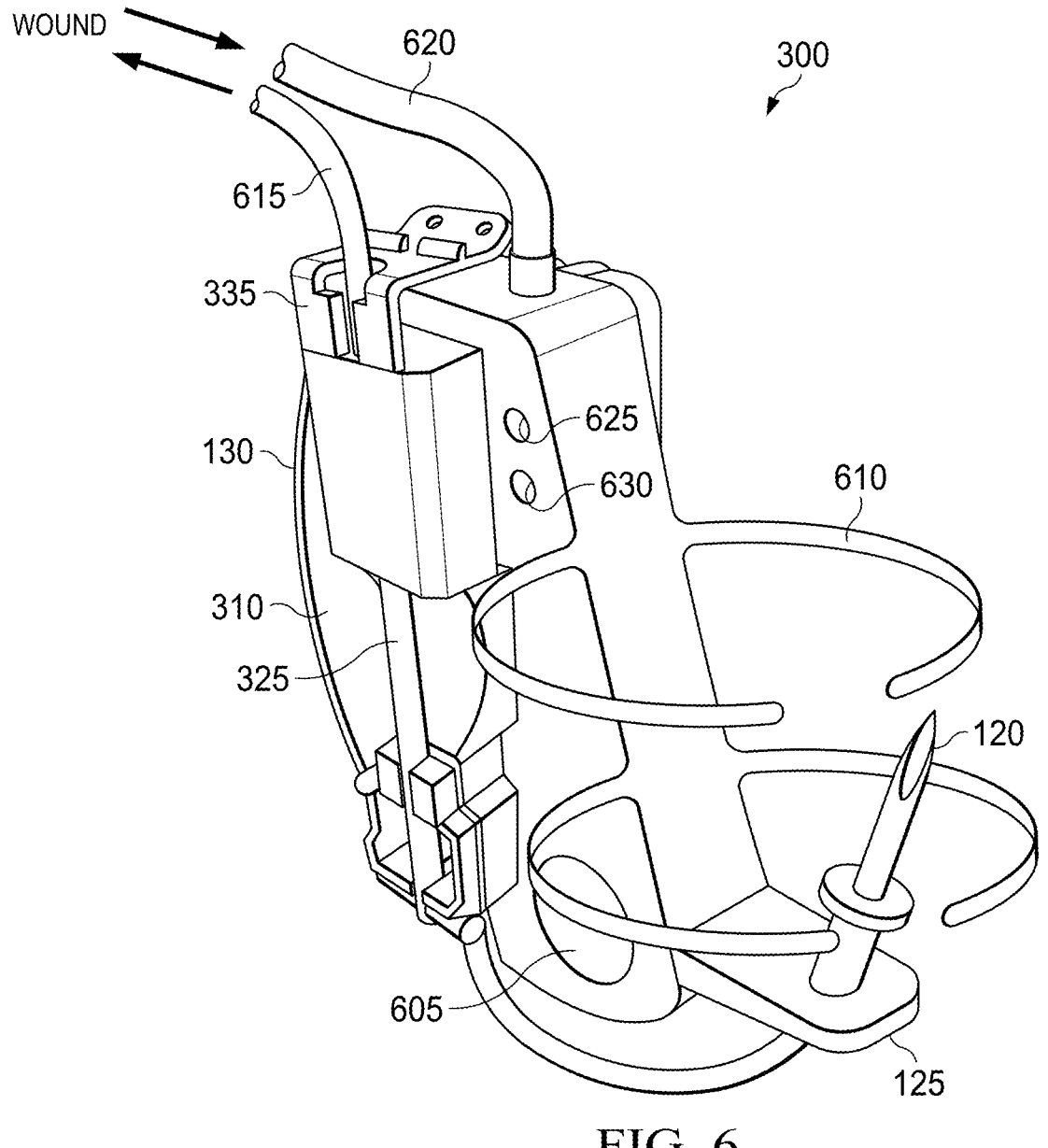
FIG. 6 illustrates a perspective view of a combined instillation fluid delivery pump head and wound fluid collection canister apparatus, according to an exemplary embodiment.

FIG. 6 illustrates a perspective view of a combined instillation fluid delivery pump head and wound fluid collection canister apparatus 300. The combined instillation fluid delivery pump head and wound fluid collection canister apparatus 300 can include the fluid spike 120, the fluid spike mount 125, the body 130, the wound fluid collection canister 310, the flexible fluid instillation conduit 325, and the latch 335 as described above.

The combined instillation fluid delivery pump head and wound fluid collection canister apparatus 300 can include a port 605. The port 605 can be disposed on the wound fluid collection canister 310 to allow exudate to drain from the wound fluid collection canister 310. The port 605 can be disposed on a wall of the wound fluid collection canister 310 and can be located in a manner that is inaccessible when the body 130 is coupled to the negative pressure wound therapy unit 150 to prevent inadvertent removal when the wound fluid collection canister 310 is in service. For example, the port 605 can be blocked by the installation fluid container 115 when the wound fluid collection canister 310 is in service. The port 605 can include a negative pressure pneumatic port. The pump motor and the negative pressure pneumatic port can be located on the same side (e.g., surface) of the negative pressure wound therapy unit 150. The port 605 can be placed against the negative pressure wound therapy unit 150 when the wound fluid collection canister 310 is fitted to the negative pressure wound therapy unit 150. The port 605 can allow a user to drain the wound exudate (e.g., collected fluids, medical waste, etc.) from the wound fluid collection canister 310. According to one embodiment, the port 605 can be 30 mm in diameter, but may be any suitable size or shape to facilitate drainage. The port 605 can allow for gelled exudate to be removed and can allow for a gel stabilizing pouch to be installed after the wound fluid collection canister 310 is emptied.

In some embodiments, the combined installation fluid delivery pump head and wound fluid collection canister apparatus 300 can include a cage 610 (e.g., installation cage, installation container cage, installation bag cage, etc.). The cage 610 can be coupled to the body 130 and configured to support the weight of the installation fluid container 115. The cage 610 can stabilize (e.g., hold, retain, etc.) the installation fluid container 115 using fingers (e.g., protrusions, flexible protrusions) that are shown to wrap around the installation fluid container 115 when the installation fluid container 115 is connected to the fluid spike 120.

The combined installation fluid delivery pump head and wound fluid collection canister apparatus 300 can include a fluid-out tube 615 (e.g. fluid delivery tube, etc.). The fluid-out tube 615 can deliver installation fluid from the installation fluid container 115 to the wound site. The combined installation fluid delivery pump head and wound fluid collection canister apparatus 300 can include a fluid-in tube 620 (e.g. fluid return tube, etc.). The fluid-in tube 620 can collect wound exudate from the wound site and deliver the wound exudate to the wound fluid collection canister 310. The fluid-in tube 620 can be coupled to the wound fluid collection canister 310 by a pneumatic connection. The combined installation fluid delivery pump head and wound fluid collection canister apparatus 300 can include a vacuum port 625. The vacuum port 625 can be coupled to the negative pressure wound therapy unit 150. The combined installation fluid delivery pump head and wound fluid collection canister apparatus 300 can include a wound fluid port 630. The wound fluid port can be coupled to the wound fluid collection canister 310.

Figure 7:
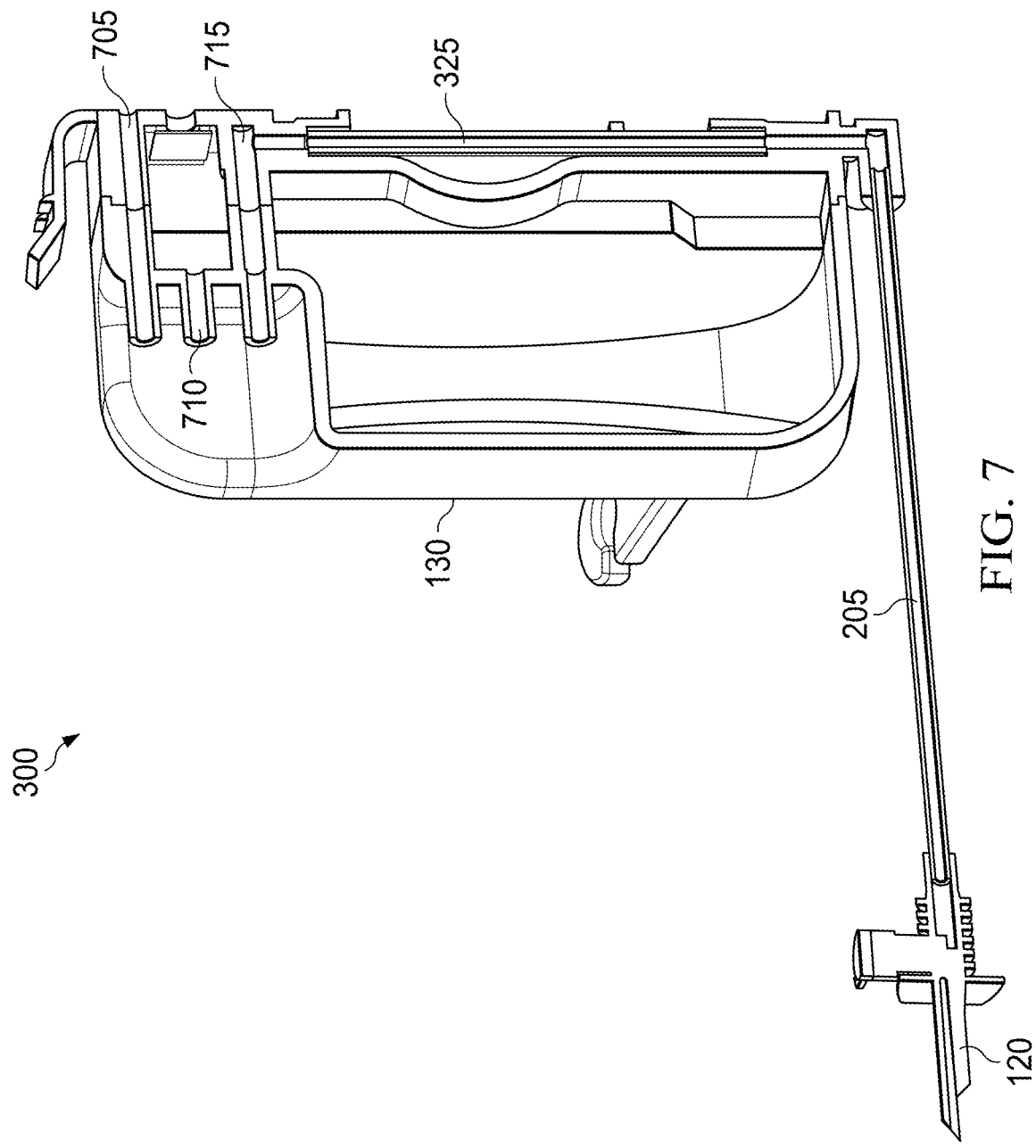
FIG. 7 illustrates a cross-sectional view of a combined instillation fluid delivery pump head and wound fluid collection canister apparatus, according to an exemplary embodiment.

FIG. 7 illustrates a cross-sectional view of a combined installation fluid delivery pump head and wound fluid collection canister apparatus 300. The combined installation fluid delivery pump head and wound fluid collection canister apparatus 300 can include a first conduit 705 (e.g., first fluid conduit, first pneumatic conduit, etc.) disposed on the body 130. The first conduit 705 can be configured to be fluidly coupled on one end of the first conduit 705 to a negative pressure source on the negative pressure wound therapy unit 150. The end of the first conduit 705 can extend through the wall of the body 130 to engage a negative pressure port on the negative pressure wound therapy unit 150. The first conduit 705 can be fluidly coupled to the wound site. The first conduit 705 can allow for pneumatic connection between the negative pressure wound therapy unit and the wound site. The first conduit 705 can be separated from the wound fluid collection canister 310. The first conduit 705 can allow for accurate (e.g., ±0.1%, ±0.5%, ±1%, ±2%, ±3%, ±4%, ±5%, etc.) wound pressure monitoring. The first conduit 705 can be free of fluids (e.g., no fluids pass up or down the first conduit 705). According to one embodiment, the first conduit 705 can be formed using an ultrasonic welding process.

The combined installation fluid delivery pump head and wound fluid collection canister apparatus 300 can include a second conduit 710 (e.g., second fluid conduit, second pneumatic conduit, etc.) disposed on the body 130. One end of the second conduit 710 can communicate with the wound fluid collection canister 310. For example, one end of the second conduit 710 can be coupled with the wound fluid collection canister 310. The second conduit 710 can be fluidly coupled to the wound fluid collection canister 310. The second conduit 710 can be fluidly coupled to the wound site. The second conduit 710 can include a fluid exudate path. For example, the second conduit 710 can include a path for wound exudate. The second conduit 710 can allow for pneumatic and fluid connection between the negative pressure wound therapy (NPWT) canister and the wound site. According to one embodiment, the second conduit 710 can be formed using an ultrasonic welding process.

The combined installation fluid delivery pump head and wound fluid collection canister apparatus 300 can also include a third conduit 715 (e.g., third fluid conduit, third pneumatic conduit, etc.) disposed on the body 130. The third conduit 715 can be fluidly coupled to one end of the flexible fluid installation conduit 325. The peristaltic pump can be configured to pump installation fluid through the third conduit 715. The third conduit 715 can be fluidly coupled to the wound site. The third conduit 715 can allow fluid (e.g., installation fluid) to travel from the fluid reservoir to the wound site. According to one embodiment, the third conduit 715 can be formed using an ultrasonic welding process.

The combined installation fluid delivery pump head and wound fluid collection canister apparatus 300 can include the flexible fluid installation conduit 325 and the fluid spike conduit 205. The flexible fluid installation conduit 325 can be fluidly coupled to the fluid spike conduit 205. The fluid spike conduit 205 can fluidly couple the fluid spike 120 to the flexible fluid installation conduit 325. The fluid spike conduit 205 can also fluidly couple the fluid spike 120 to the third conduit 715.

Figure 8:
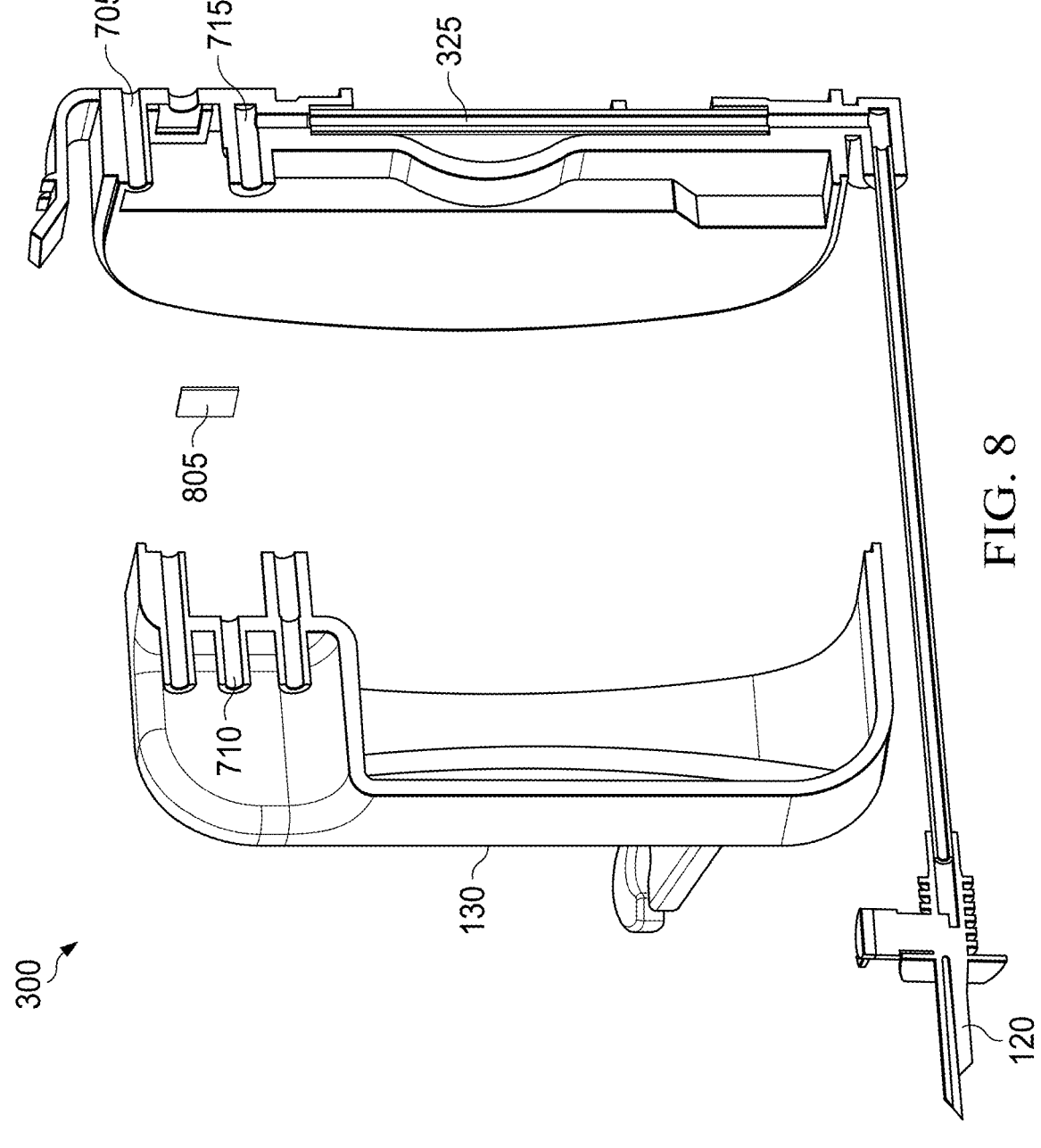
FIG. 8 illustrates an exploded view of the combined instillation fluid delivery pump head and wound fluid collection canister apparatus of FIG. 7, according to an exemplary embodiment.

FIG. 8 illustrates an exploded view of the combined installation fluid delivery pump head and wound fluid collection canister apparatus 300 of FIG. 7, illustrating an exemplary configuration of the first conduit 705, the second conduit 710, the third conduit 715, the body 130, and the flexible fluid installation conduit 325 as described above.

The combined installation fluid delivery pump head and wound fluid collection canister apparatus 300 can include a filter 805. The filter 805 can be disposed between the second conduit 710 and the wound fluid collection canister 310 to prevent liquid or solid particles from reaching the negative pressure wound therapy unit. The filter 805 can include, for example, a bacterial filter that is hydrophobic and/or lipophilic such that aqueous and/or oily liquids will be on the surface of the filter 805.

Figure 9:
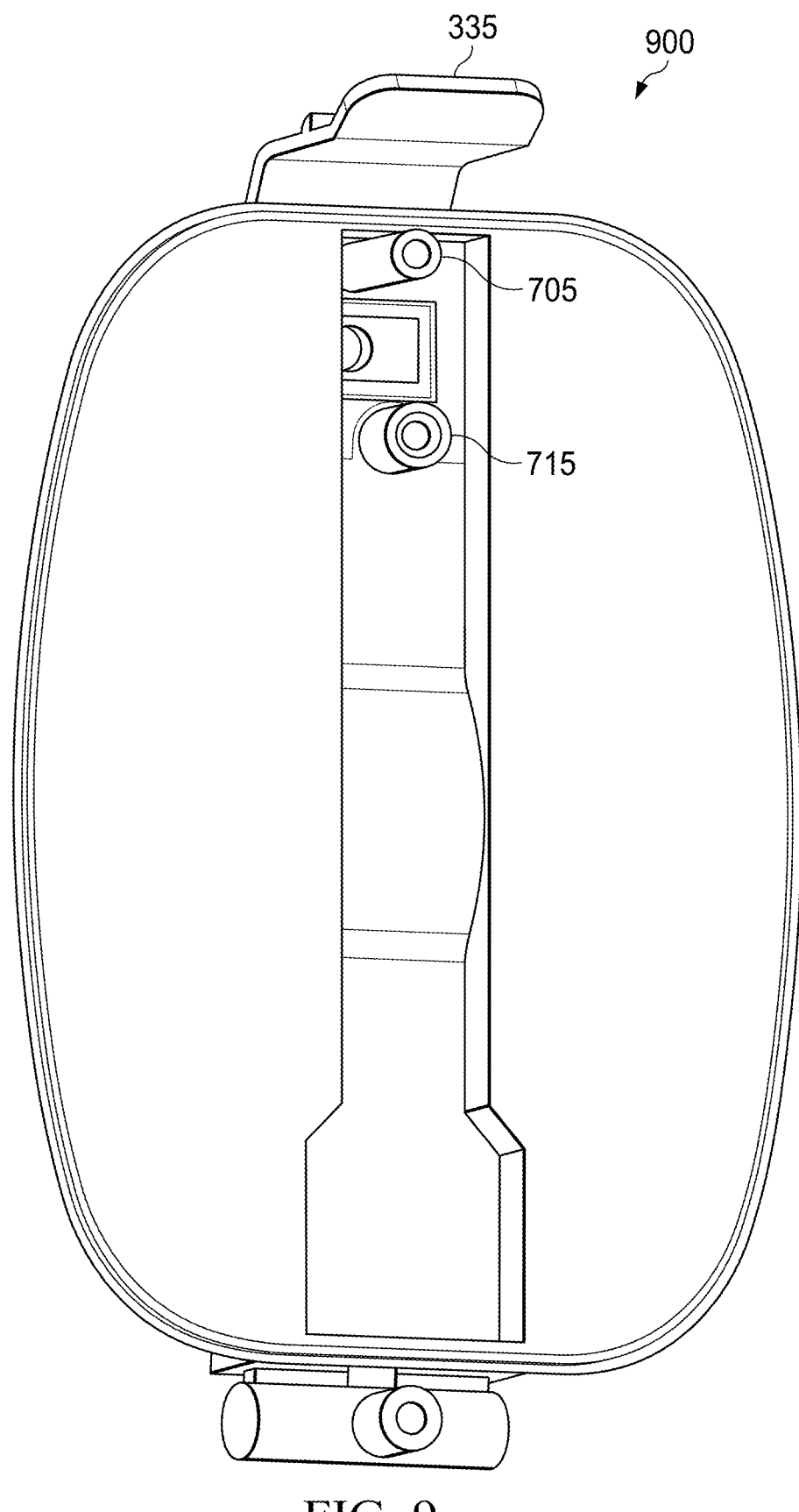
FIGS. 9 and 10 illustrate perspective views of a canister base, according to an exemplary embodiment.
Figure 10:
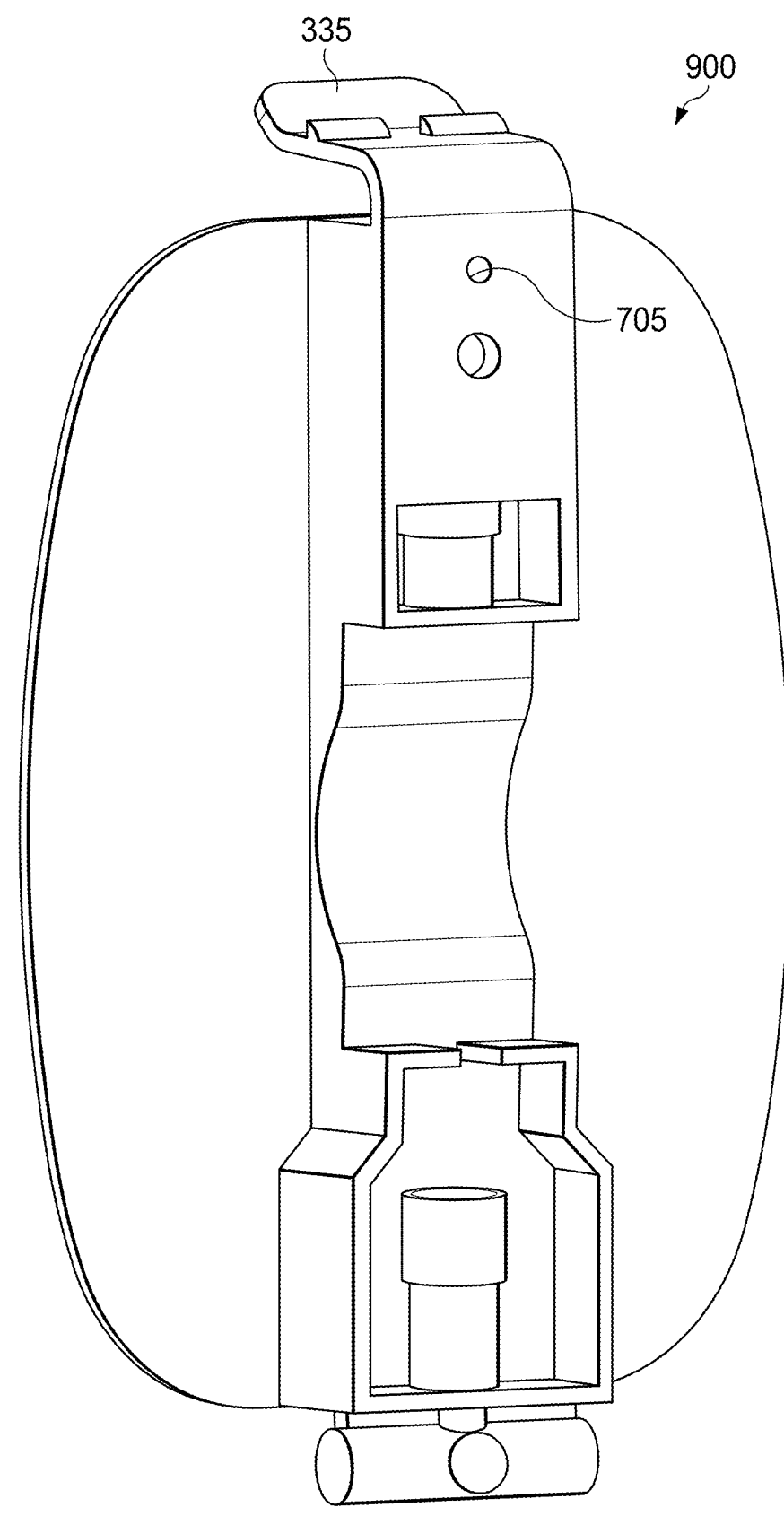
Figure 11:
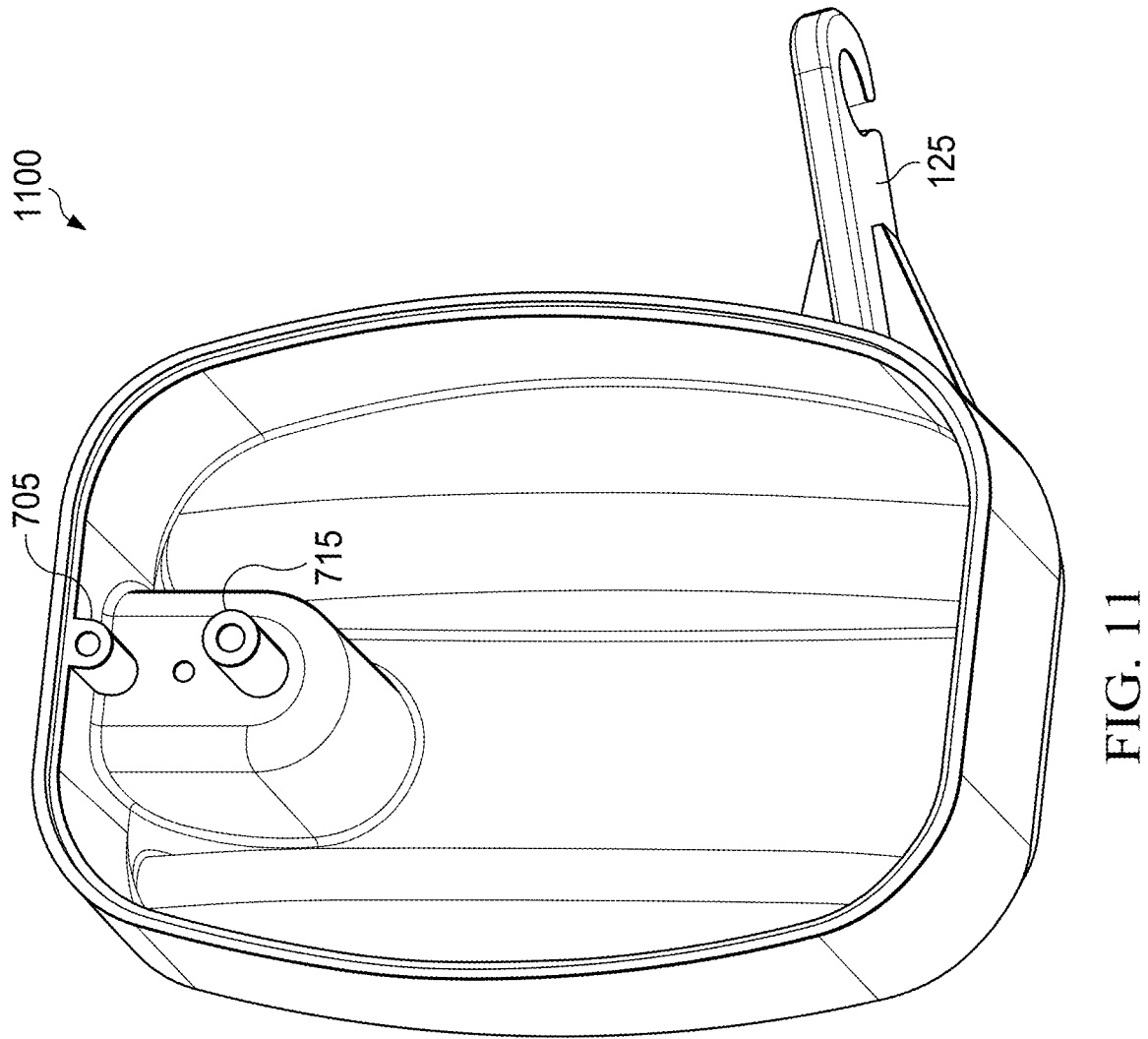
FIGS. 11-14 illustrate perspective views of a canister body, according to an exemplary embodiment.
Figure 12:
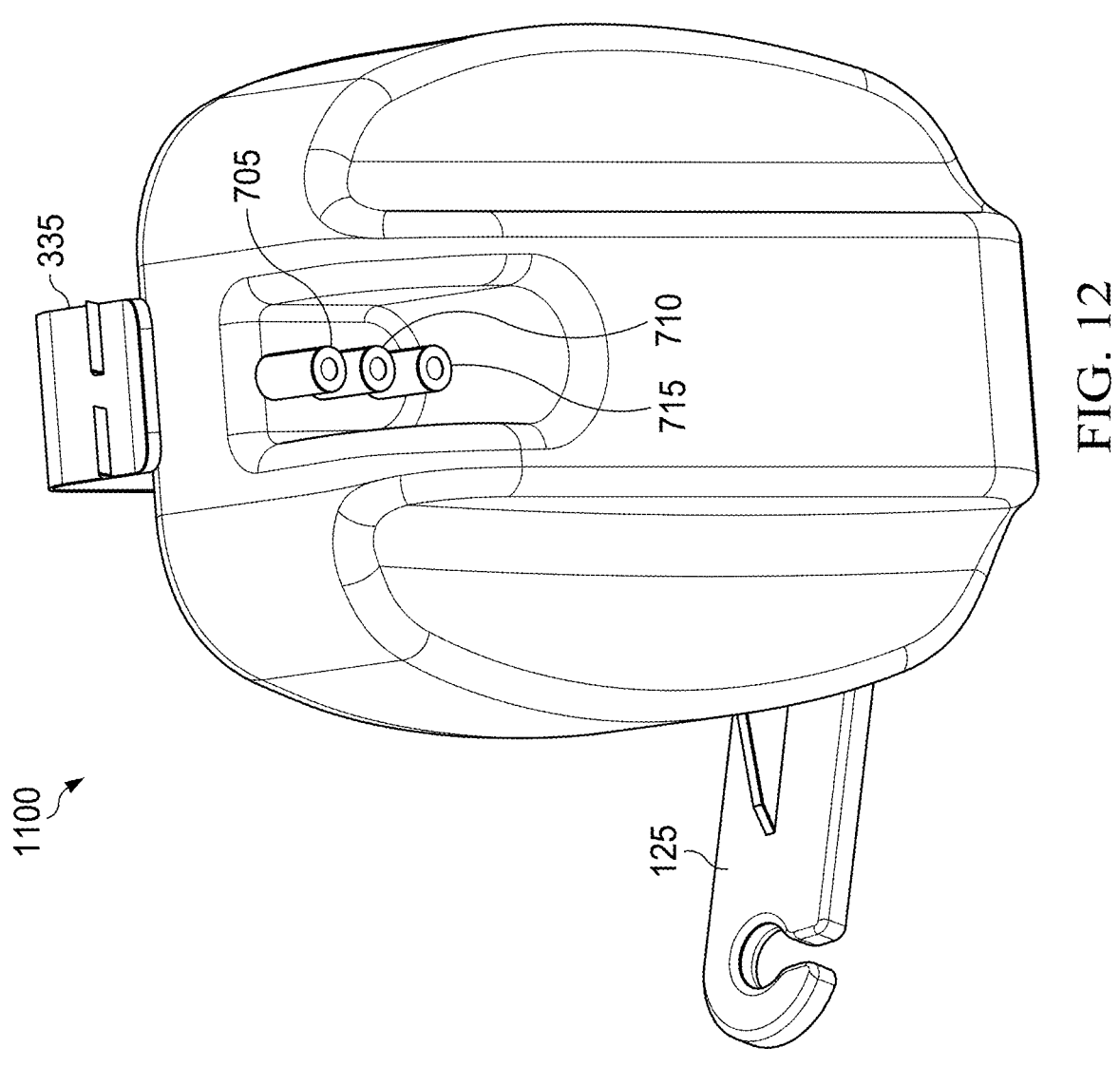
Figure 13:
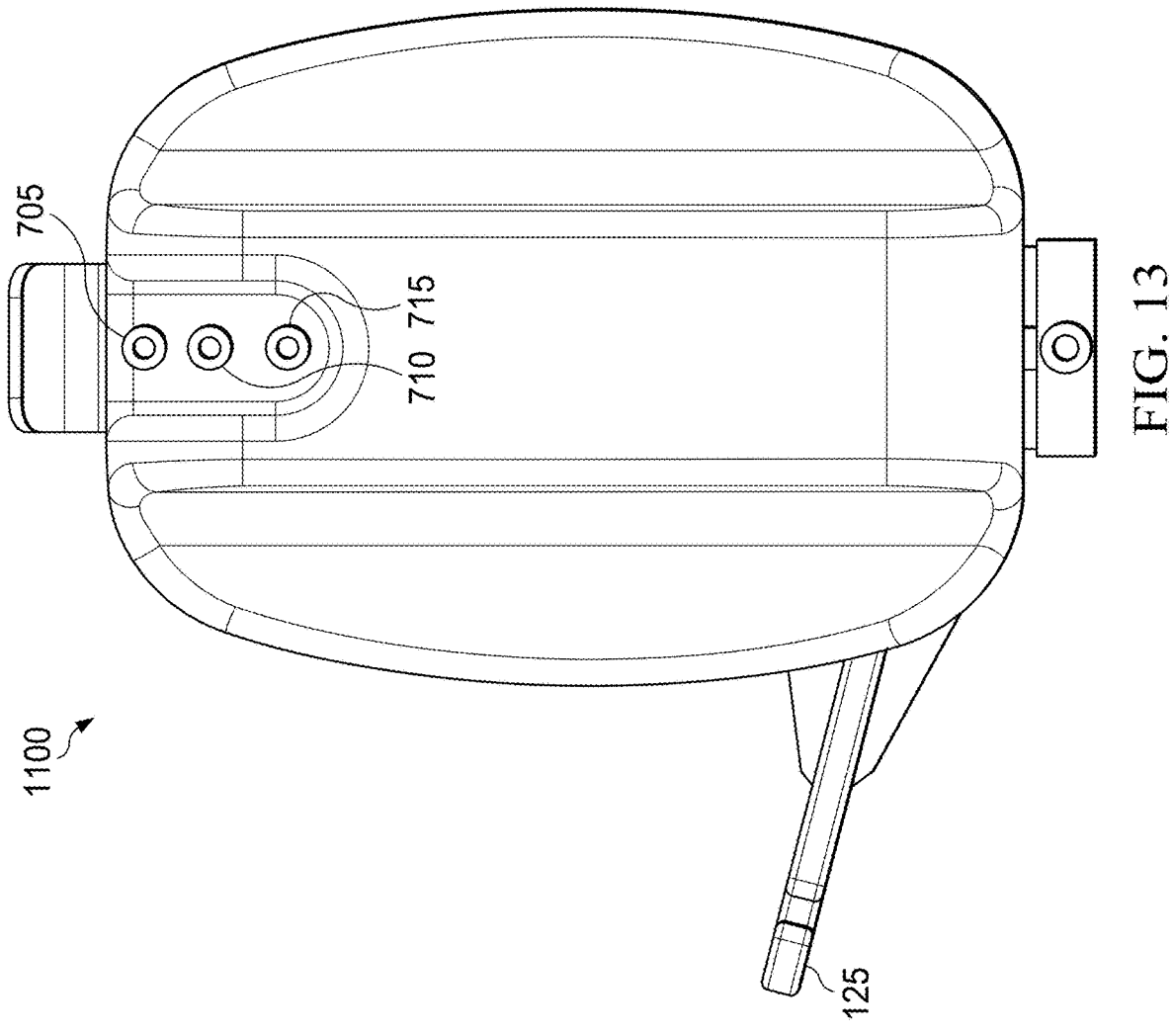
Figure 14:
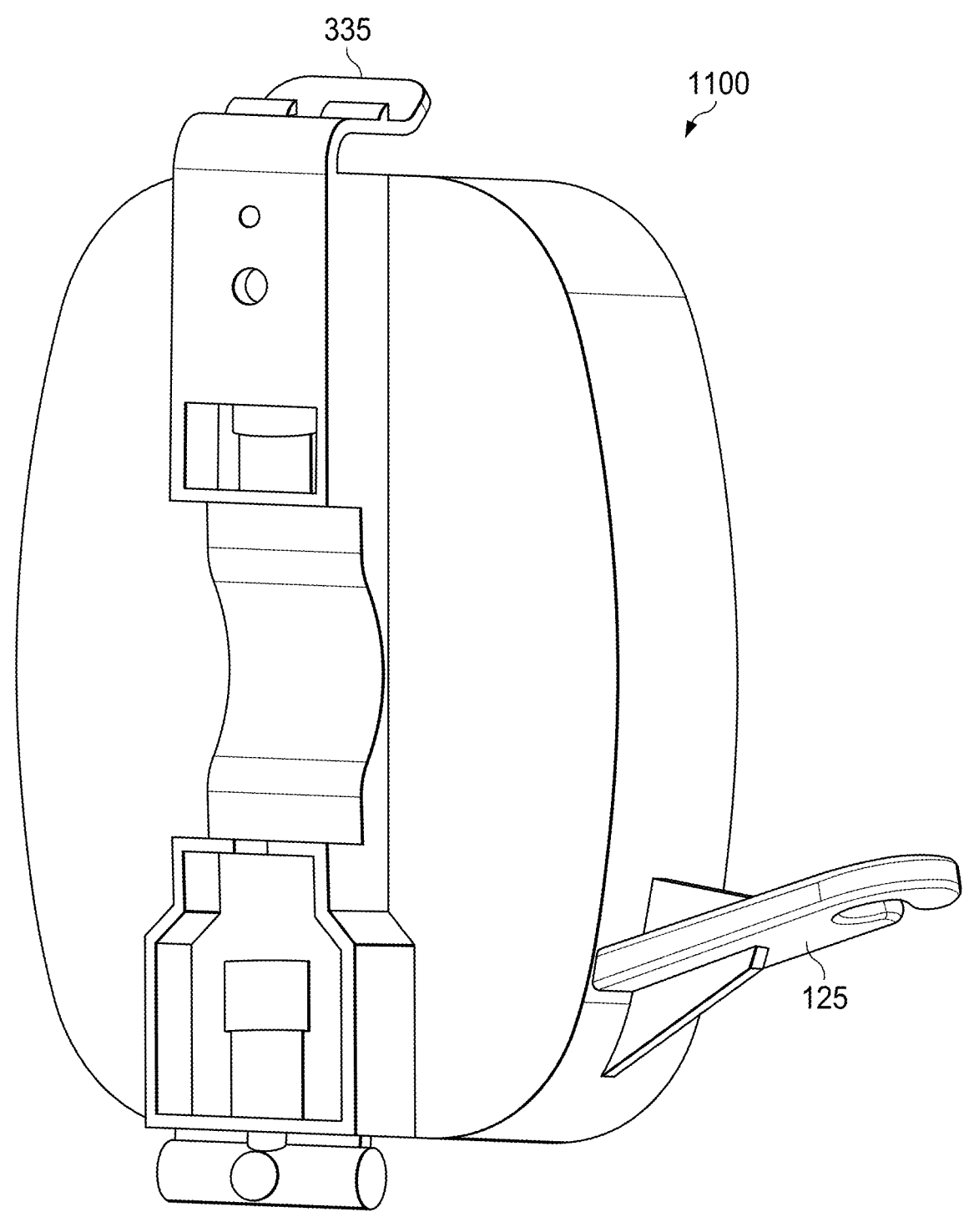

FIGS. 9 and 10 illustrate perspective views of a canister base 900. The canister base 900 can include the latch 335, the first conduit 705, and the third conduit 715 as described above. The canister base 900 can be configured to couple with the body 130. The first conduit 705 can be disposed between the latch 335 and the third conduit 715. The first conduit 705 and the third conduit 715 can be disposed on an upper portion (e.g., upper half, top half, etc.) of the canister base 900. The latch 335 can be disposed on an end of the canister base 900. The canister base 900 can form a part of the wound fluid collection canister 310.

FIGS. 11-14 illustrate perspective views of a canister body 1100 (e.g., body 130). The canister body 1100 can include the fluid spike mount 125, the latch 335, the first conduit 705, the second conduit 710, and the third conduit 715. The first conduit 705 can be disposed between the second conduit 710 and the latch 335. The second conduit 710 can be disposed between the first conduit 705 and the third conduit 715. The third conduit 715 can be disposed between the first conduit 705 and the second conduit 710. The first conduit 705 can be disposed between the second conduit 710 and the third conduit 715. The first conduit 705, second conduit 710, and the third conduit 715 can be disposed on an upper portion (e.g., upper half, top half, etc.) of the canister body 1100. The first conduit 705, second conduit 710, and the third conduit 715 can be disposed on an interior of the canister body 1100. The fluid spike mount 125 can be disposed on an exterior lower portion (e.g., lower half, bottom half, etc.) of the canister body 1100. The canister body 1100 can form a part of the wound fluid collection canister 310.

Figure 15:
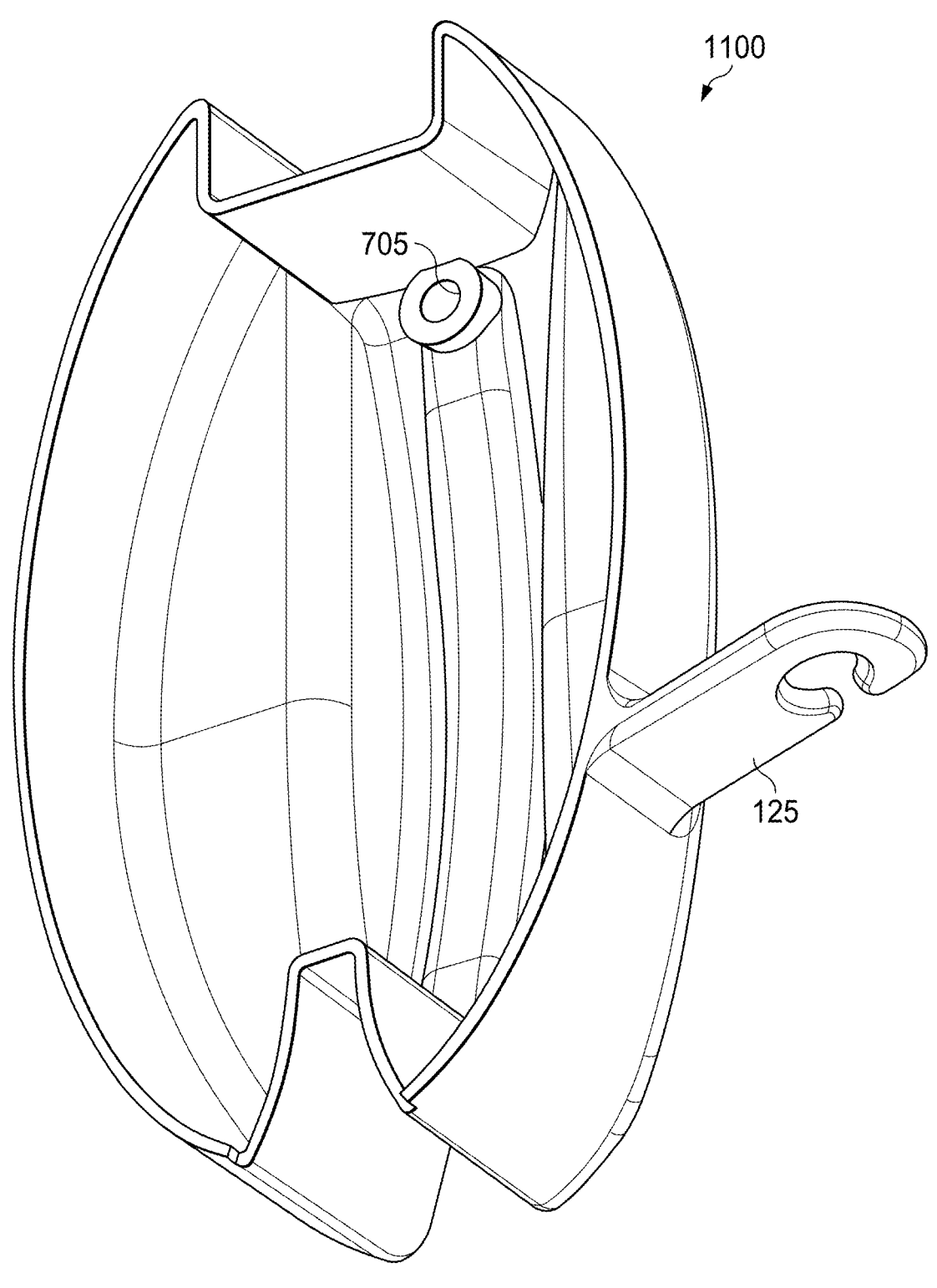
FIGS. 15 and 16 illustrate perspective views of a canister body, according to an exemplary embodiment.
Figure 16:
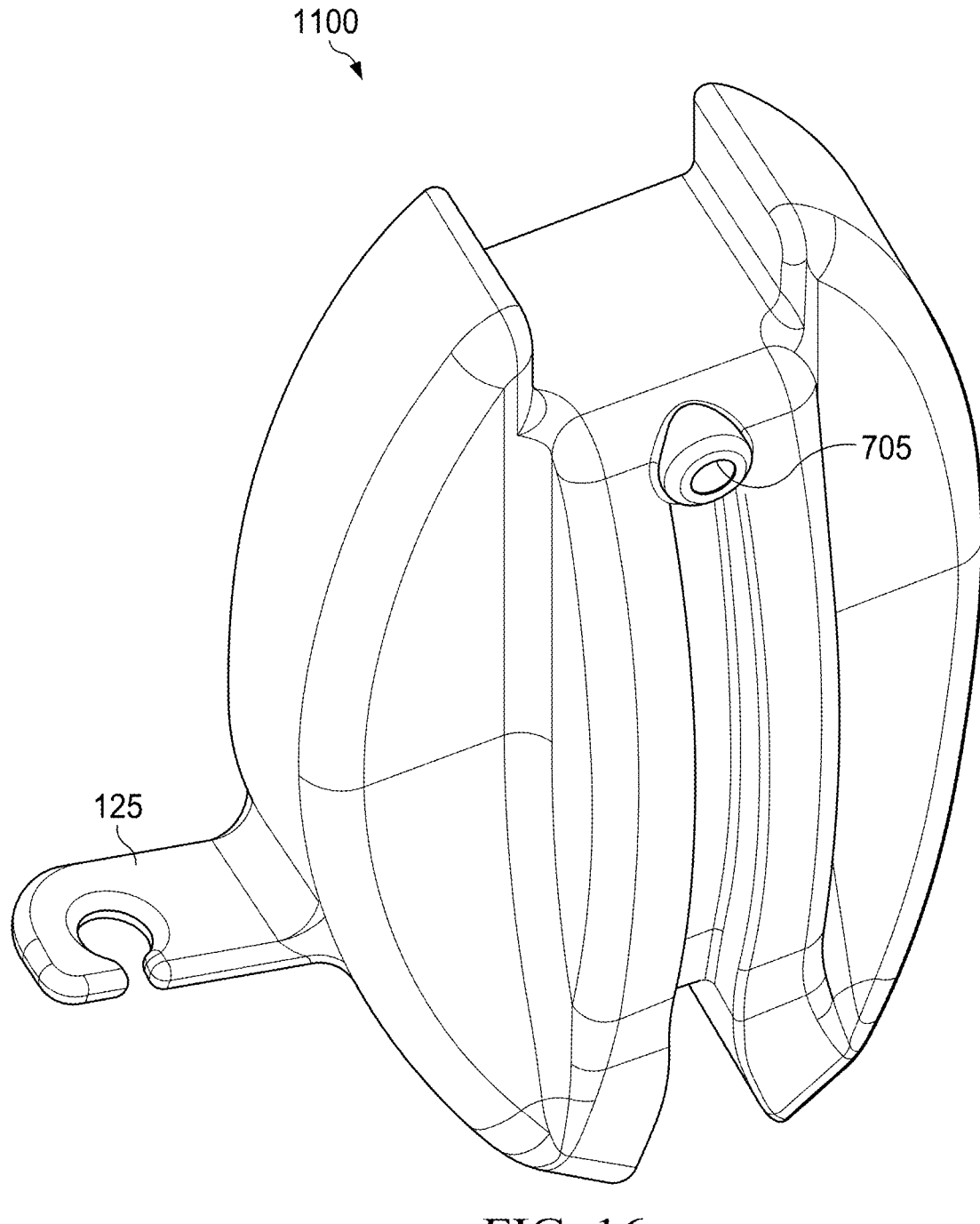

FIGS. 15 and 16 illustrate perspective views of the canister body 1100 (e.g., body 130). The canister body 1100 can include the fluid spike mount 125 and the first conduit 705 as described above. The first conduit 705 can be disposed on an upper portion (e.g., upper half, top half, etc.) of the canister body 1100. The first conduit 705 can be disposed on an exterior of the canister body 1100. The fluid spike mount 125 can be disposed on an exterior lower portion (e.g., lower half, bottom half, etc.) of the canister body 1100. The canister body 1100 can have a shape profile configured to mate with the canister base 900.

Figure 17:
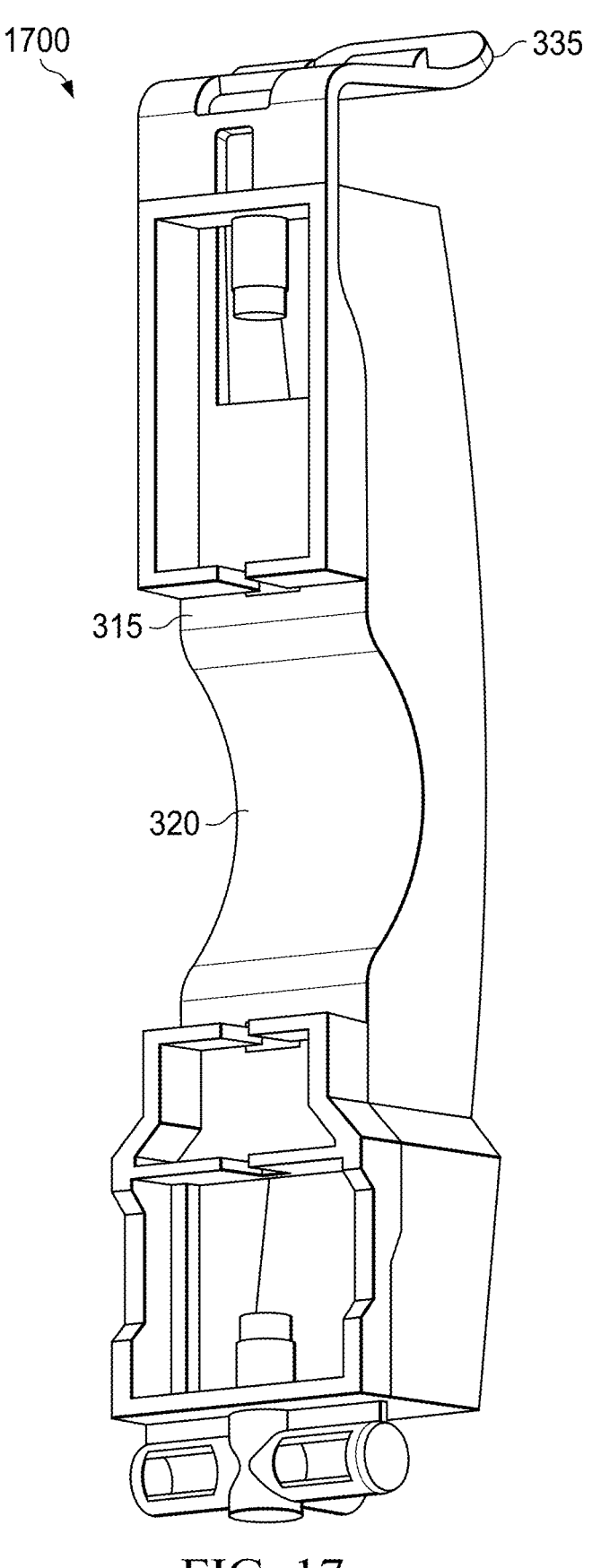
FIGS. 17 and 18 illustrate perspective views of an attachment mechanism, according to an exemplary embodiment.
Figure 18:
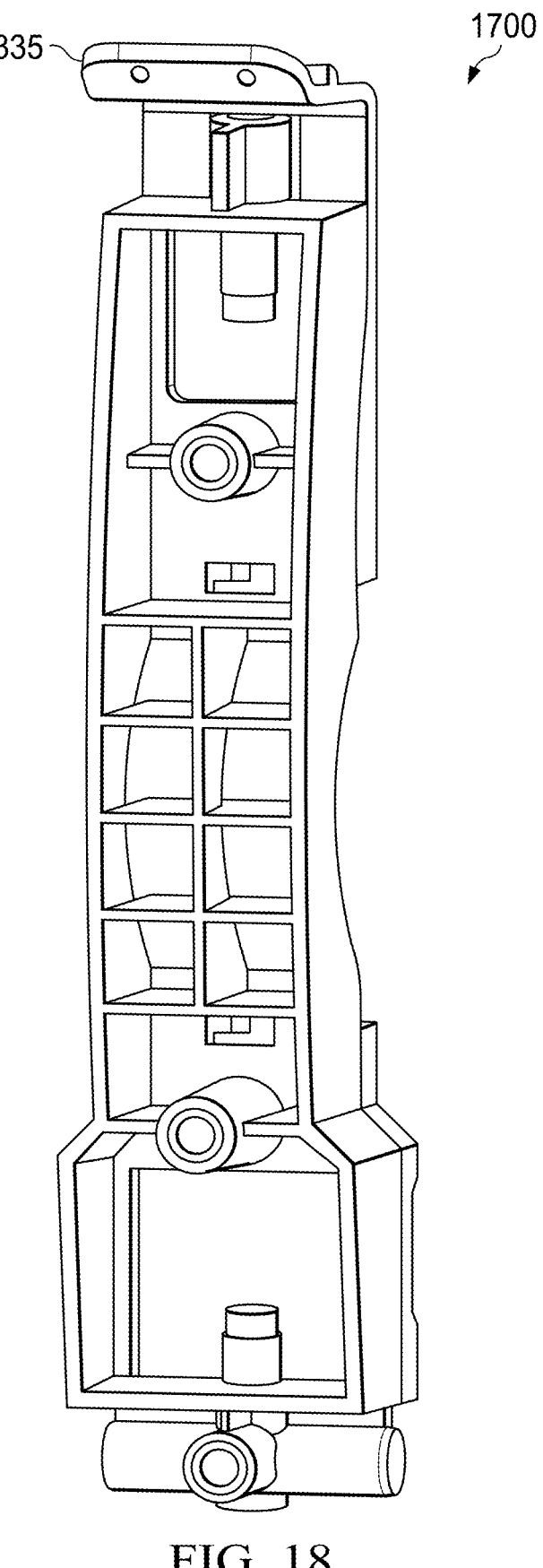

FIGS. 17 and 18 illustrate perspective views of an attachment mechanism 1700. The attachment mechanism 1700 can include the latch 335, the pump head 315, and the recess 320 as described above, and can couple with the body 130. The attachment mechanism 1700 is intended to support the weight of the installation fluid container 115 and the wound fluid collection canister 310. The attachment mechanism 1700 can couple with the canister body 1100, the canister base 900, and/or the negative pressure wound therapy unit 150

Figure 19:
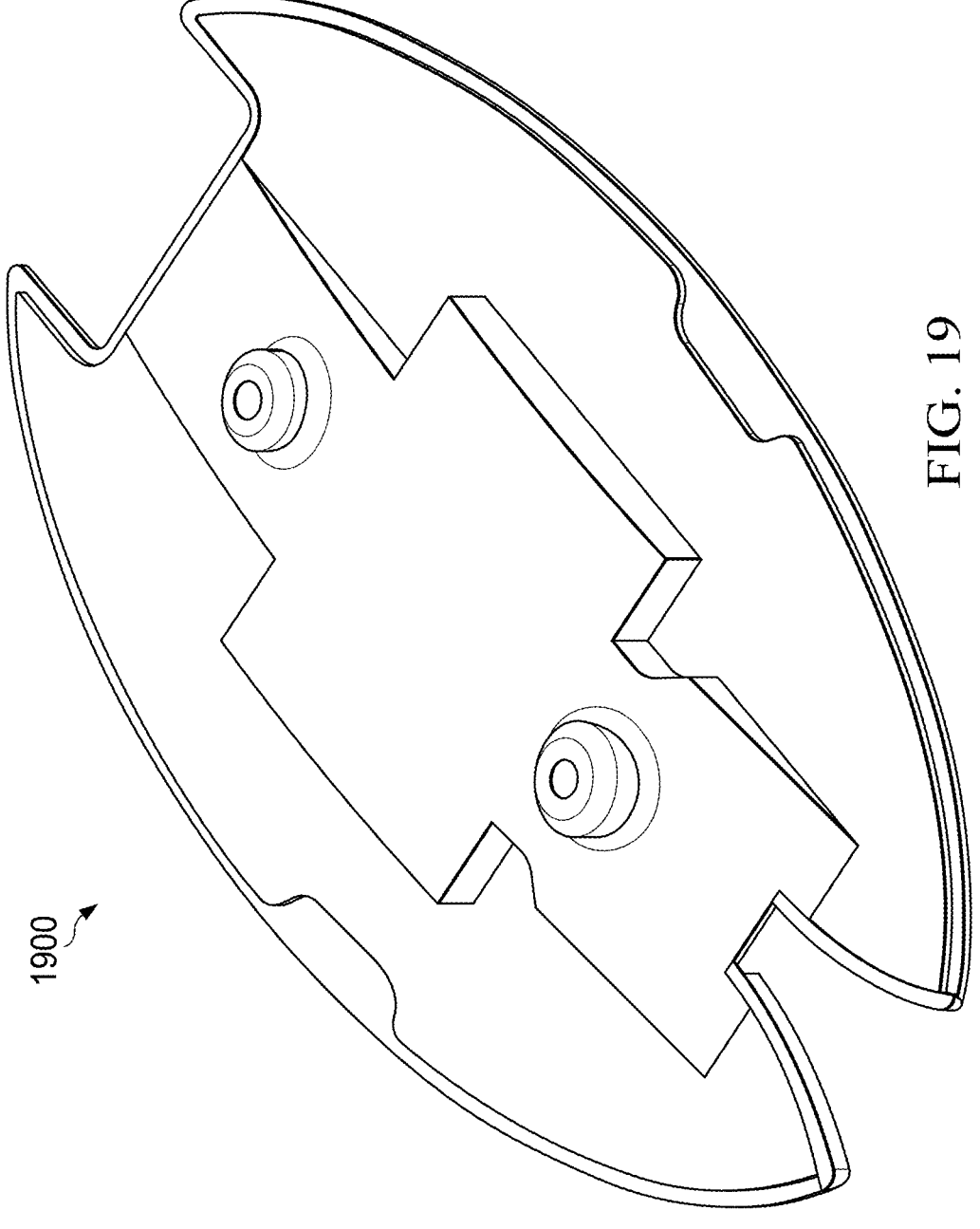
FIG. 19 illustrates a perspective view of a canister lid, according to an exemplary embodiment.

FIG. 19 illustrates a perspective view of a canister lid 1900 (e.g., canister cover, removable cover, removable canister lid, removable canister cover, etc.). The canister lid 1900 is intended to couple with the wound fluid collection canister 310. The canister lid 1900 can be shaped such that the canister lid 1900 interlocks with the wound fluid collection canister 310. The canister lid 1900 combined with the wound fluid collection canister 310 can provide a container for collecting wound fluid exudate. The canister lid 1900 can be removably attachable to the wound fluid collection canister 310 by a cable and/or tether. The canister lid 1900 can also be colored such that the canister lid 1900 stands out to a user. The canister lid 1900 can be configured to couple with the canister base 900, and/or with the canister body 1100.

Figure 20:
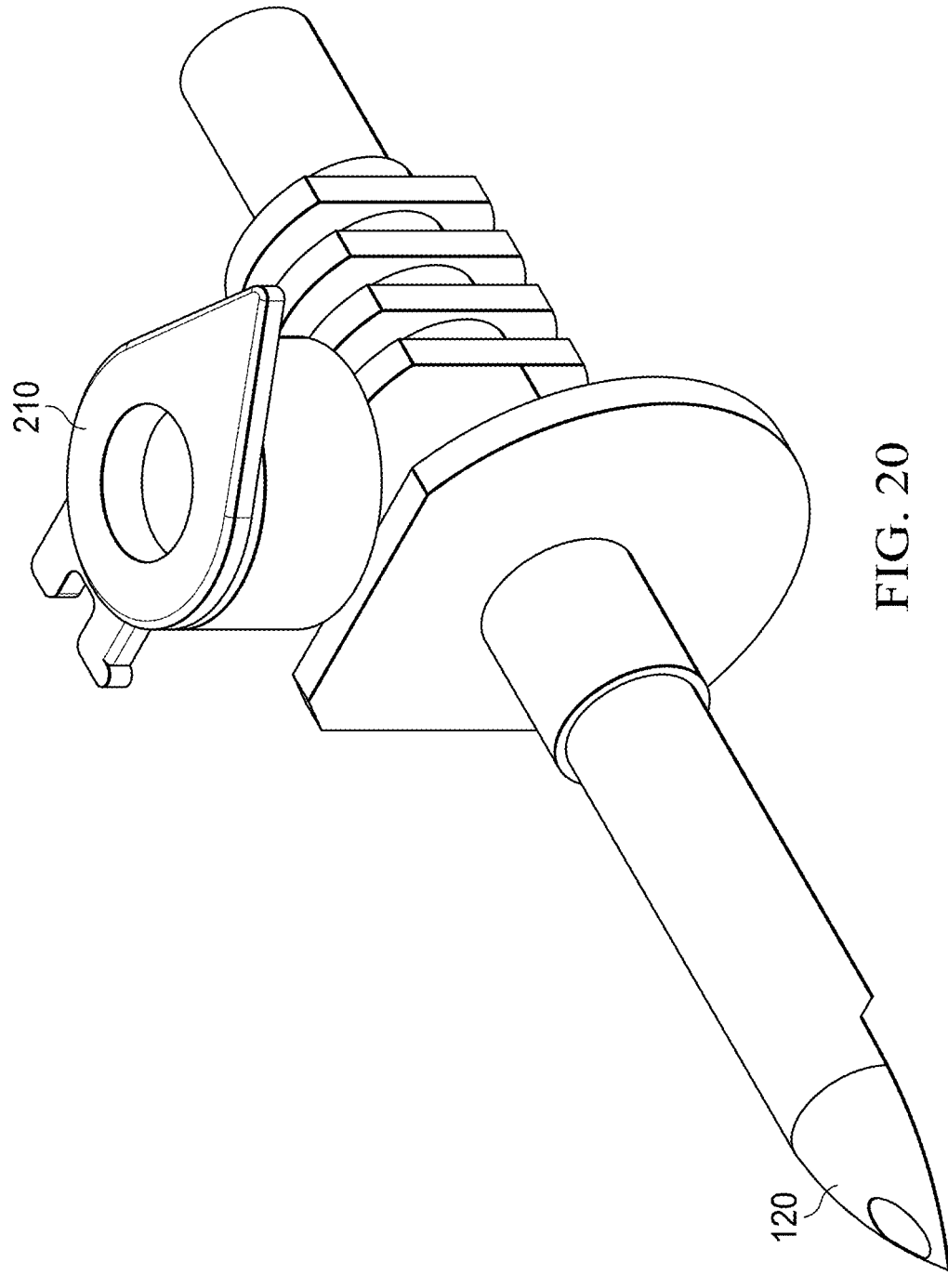
FIG. 20 illustrates a perspective view of a fluid spike, according to an exemplary embodiment.

FIG. 20 illustrates a perspective view of the fluid spike 120 (e.g., spike, fluid container connection spike, spike head, integrated fluid storage bag spike, fluid bag connection spike, pre-fitted installation bag spike, etc.). The fluid spike 120 can be configured to couple (e.g., connect, affix, link, join, etc.) to the installation fluid container 115. For example, the fluid spike 120 can be removably connected to the installation fluid container 115. The fluid spike 120 can be configured to pierce (e.g., puncture) the installation fluid container 115. For example, the fluid spike 120 can pierce the installation fluid container 115 such that installation fluid is accessible to the installation and exudate unit 105. The fluid spike 120 can have a sharp end configured to pierce the installation fluid container 115 in order to fluidly couple the installation fluid container 115 to the installation and exudate unit 105. The fluid spike 120 can include a cavity configured to allow installation fluid to flow. The fluid spike 120 can also include the valve 210 configured to control (e.g., regulate, direct, etc.) the flow of installation fluid from the installation fluid container 115. The valve 210 can be disposed on the fluid spike 120, or between the fluid spike 120 and the fluid spike conduit 205 and can regulate the flow of installation fluid through the fluid spike conduit 205 (e.g. by opening, closing, or partially obstructing the fluid spike conduit 205).

Figure 21:
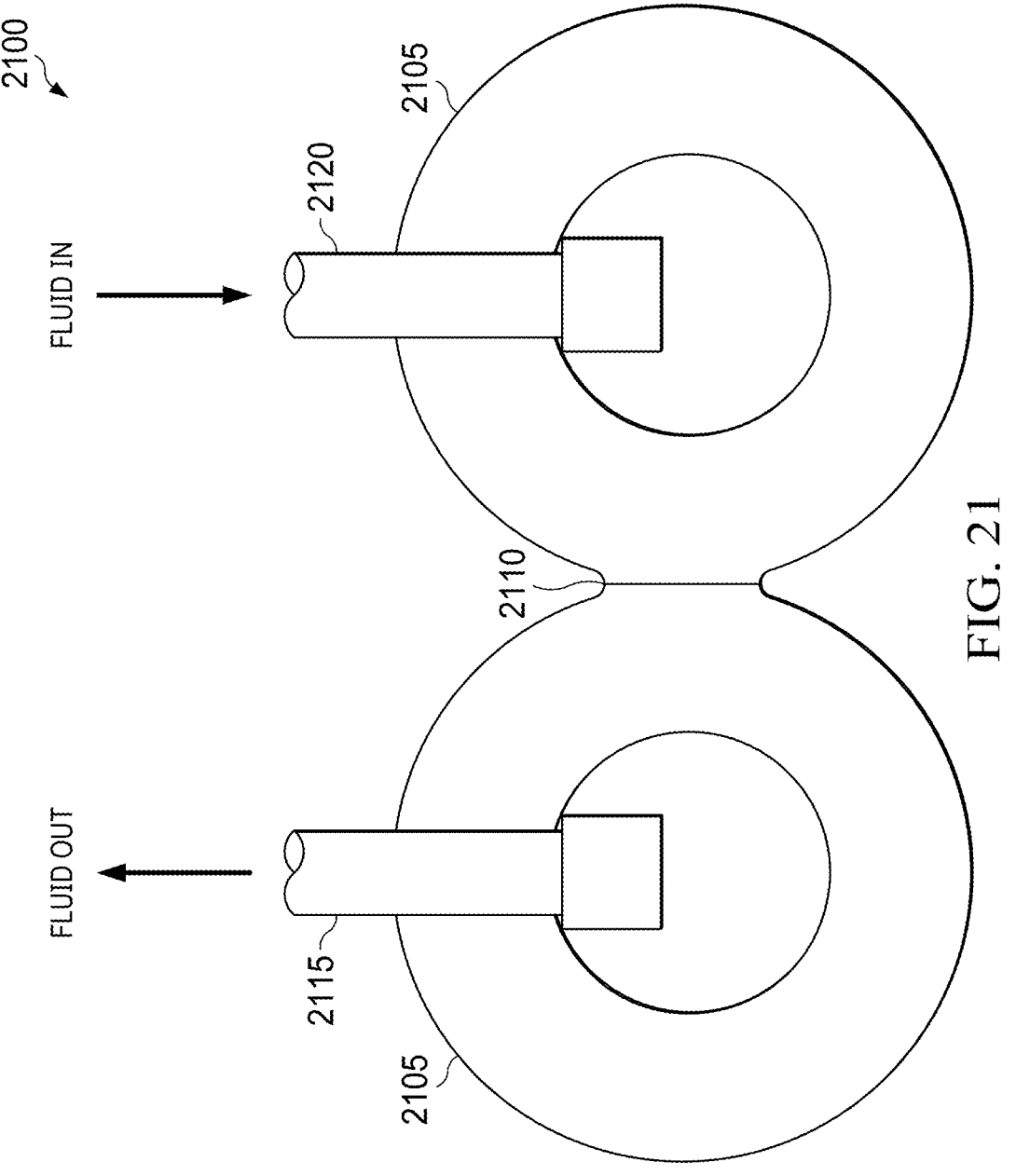
FIG. 21 illustrates a perspective view of a combined pad and tubing apparatus, according to an exemplary embodiment.

FIG. 21 illustrates a perspective view of a combined pad and tubing apparatus 2100 (e.g., combined extruded tube set). The combined pad and tubing apparatus 2100 can include one or more pads 2105. In some embodiments, the one or more pads 2105 may be connected to each other. The one or more pads 2105 can also be connected by a perforated boundary 2110 to permit separation. The one or more pads 2105 can include an adhesive under the one or more pads 2105 or pad flanges to allow the one or more pads 2105 to be attached to the dressing and/or wound site. The combined pad and tubing apparatus 2100 is shown to include a fluid-out tube 2115 (e.g., fluid-delivery tube or fluid-out tube 615). The fluid-out tube 2115 can be fluidly coupled to the first conduit 705. In some embodiments, the fluid-out tube 2115 can be fluidly coupled to the second conduit 710 and/or the third conduit 715. The combined pad and tubing apparatus 2100 can include a fluid-in tube 2120 (e.g., fluid-return tube or fluid-in tube 620). The fluid-in tube 2120 can be fluidly coupled to the third conduit 715. In some embodiments, the fluid-in tube 2120 can be fluidly coupled to the first conduit 705 and/or the second conduit 710.

The combined installation fluid delivery pump head and wound fluid collection canister apparatus 300 can include a multi-lumen tube element comprising a first lumen, a second lumen, and a third lumen. The first lumen can be configured to fluidly couple the first conduit 705 to a dressing and/or wound site and can be part of the fluid-out tube 2115. The second lumen can be configured to fluidly couple the second conduit 710 to the dressing and/or wound site. The third lumen can be configured to couple the third conduit 715 to the dressing and/or wound site and can be a part of the fluid-in tube 2120. The multi-lumen tube element can be co-extruded tubes. The co-extruded tubes can be separated by a user. For example, the co-extruded tubes can be attached by a thin web that can break if force is exerted to allow a user to pull apart the co-extruded tubes. Additionally, the co-extruded tubes can be pulled apart to change the location of each pad of the one or more pads 2105.

Figure 22:
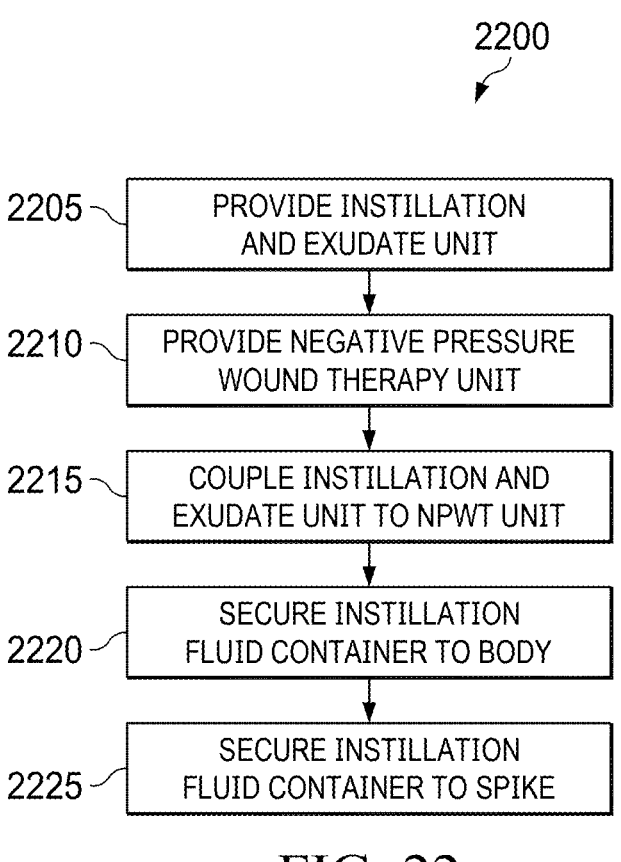
FIG. 22 illustrates a block diagram of an example method for providing instillation and negative pressure wound therapy, according to an exemplary embodiment.

FIG. 22 illustrates a block diagram of an example method 2200 for providing installation and negative pressure wound therapy. In brief summary, the method 2200 can include providing an installation and exudate unit 2205. The method 2200 can include providing a negative pressure wound therapy unit 2210, coupling the installation and exudate unit to the negative pressure wound therapy unit 2215, securing an installation fluid container to the installation and exudate unit 2205 (such as but not limited to positioning within a cage 2220). The method 2200 can include securing the installation fluid container to a fluid spike 2225.

The method 2200 can also include providing an installation and exudate unit 2205 that includes a body defining a wound fluid collection canister. The wound fluid collection canister can be configured to collect wound exudate. The body can also define a pump head formed by a partially cylindrical recess in a wall of the body. The installation and exudate unit can include a flexible fluid installation conduit extending along the pump head. The flexible fluid installation conduit can be configured to be compressed by a pump rotor. The installation and exudate unit can include a first conduit disposed on the body and fluidly coupled on one end of the first conduit to a negative pressure source. The installation and exudate unit can include a second conduit disposed on the body with one end of the second conduit communicating with the wound fluid collection canister. The installation and exudate unit can also include a third conduit disposed on the body and fluidly coupled to one end of the flexible fluid installation conduit. A port may be disposed on the installation and exudate unit between the wound fluid collection canister and the negative pressure wound therapy unit. The port can be configured to allow exudate to drain from the wound fluid collection canister.

The method 2200 can also include providing a negative pressure wound therapy unit 2210 coupled to the installation and exudate unit. The negative pressure wound therapy unit can include a peristaltic pump configured to pump installation fluid through the third conduit. The method 2200 can also include disposing an installation fluid container and the wound fluid collection canister on a side of the negative pressure wound therapy unit. The installation fluid container and the wound fluid collection canister can be disposed on the same side of the negative pressure wound therapy unit. In some embodiments, the installation fluid container and the wound fluid collection canister can be disposed on different sides of the negative pressure wound therapy unit.

The method 2200 can also include coupling the installation and exudate unit to the negative pressure wound therapy unit 2215 by an attachment mechanism. According to one embodiment, the attachment mechanism may be or comprise a latch disposed on the body.

The method 2200 can also include securing an installation fluid container to the body. For example, the installation fluid container can be disposed in the cage coupled to or integrally formed with the body. The installation fluid container can be removably positioned in the cage. The cage is intended to support the weight of the installation fluid container.

The method 2200 can also include securing the installation fluid container to a fluid spike 2225. The fluid spike can be coupled to the wound fluid collection canister. The fluid spike can pierce the installation fluid container. The fluid spike can be secured to the installation fluid container by piercing installation fluid container with the fluid spike.

Any references to implementations or elements or acts of the systems and methods herein referred to in the singular can include implementations including a plurality of these elements, and any references in plural to any implementation or element or act herein can include implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementations," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and Elements other than 'A' and 'B' can also be included.

The systems and methods described herein may be embodied in other specific forms without departing from the characteristics thereof. The foregoing implementations are illustrative rather than limiting of the described systems and methods.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An installation and negative pressure wound therapy apparatus comprising:
   an installation and exudate unit comprising:
      a body defining a wound fluid collection canister configured to collect wound exudate and defining a pump head formed by a partially cylindrical recess in a wall of the body;
      a flexible fluid installation conduit extending along the pump head and configured to be compressed by a pump rotor, the flexible fluid installation conduit having a first end coupled to a first port formed by the wall and a second end coupled to a second port formed by the wall, the first port and the second port on opposing sides of the partially cylindrical recess in the wall;
      a first conduit disposed on an interior of the body and configured to be fluidly coupled on one end of the first conduit to a negative pressure source and on another end to a wound site;
      a second conduit disposed on the body and having one end of the second conduit communicating with the wound fluid collection canister and on a second end to a wound site; and
      a third conduit disposed on the body and fluidly coupled to the flexible fluid installation conduit through the first port;
   a negative pressure wound therapy unit coupled to the installation and exudate unit, the negative pressure wound therapy unit further comprising:

a peristaltic pump configured to pump instillation fluid through the third conduit and configured to compress the flexible fluid instillation conduit.

2. The apparatus of claim 1, further comprising: a port disposed on the wound fluid collection canister and configured to allow exudate to drain from the wound fluid collection canister.

3. The apparatus of claim 1, further comprising: an attachment mechanism configured to couple the instillation and exudate unit to the negative pressure wound therapy unit.

4. The apparatus of claim 1, further comprising:

a multi-lumen tube element comprising a first lumen, a second lumen, and a third lumen;

wherein the first lumen is configured to fluidly couple the first conduit to a dressing, the second lumen is configured to fluidly couple the second conduit to the dressing, and the third lumen is configured to couple the third conduit to the dressing.

* * * * *